United States Patent
Shikii et al.

(10) Patent No.: US 11,037,425 B2
(45) Date of Patent: Jun. 15, 2021

(54) SLEEPINESS ESTIMATING DEVICE, WAKEFULNESS INDUCTION CONTROL DEVICE, AND WAKEFULNESS INDUCTION SYSTEM

(71) Applicant: PANASONIC INTELLECTUAL PROPERTY MANAGEMENT CO., LTD., Osaka (JP)

(72) Inventors: Shinichi Shikii, Nara (JP); Koichi Kusukame, Nara (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 16/616,383

(22) PCT Filed: May 24, 2018

(86) PCT No.: PCT/JP2018/019925
§ 371 (c)(1),
(2) Date: Nov. 22, 2019

(87) PCT Pub. No.: WO2018/221364
PCT Pub. Date: Dec. 6, 2018

(65) Prior Publication Data
US 2020/0082700 A1 Mar. 12, 2020

(30) Foreign Application Priority Data
May 30, 2017 (JP) .............................. JP2017-107014

(51) Int. Cl.
*G08B 23/00* (2006.01)
*G08B 21/06* (2006.01)
(Continued)

(52) U.S. Cl.
CPC ................ *G08B 21/06* (2013.01); *A61B 5/16* (2013.01); *A61B 5/4809* (2013.01); *G06K 9/00624* (2013.01)

(58) Field of Classification Search
CPC .... A61B 5/16; A61B 5/18; A61B 5/01; A61B 5/4809; A61B 5/7278; A61B 2560/0242;
(Continued)

(56) References Cited

U.S. PATENT DOCUMENTS

| 4,928,090 A | * | 5/1990 | Yoshimi | ................... A61B 5/18 340/575 |
| 5,682,882 A | * | 11/1997 | Lieberman | ............. G08B 21/06 600/301 |

(Continued)

FOREIGN PATENT DOCUMENTS

| JP | H10-315800 A | 12/1998 |
| JP | H11-109985 A | 4/1999 |

(Continued)

OTHER PUBLICATIONS

Extended European Search Report dated Apr. 22, 2020 issued in corresponding European Patent Patent Application No. 18809721.6.
(Continued)

*Primary Examiner* — Toan N Pham
(74) *Attorney, Agent, or Firm* — McDermott Will and Emery LLP

(57) ABSTRACT

A sleepiness estimating device includes an environmental information detector that detects a plurality of conditions of an environment surrounding a user and outputs environmental information indicating the detected conditions of the environment, a calculator that calculates an environmental level indicating a degree of how likely the user becomes sleepy in the environment in accordance with the environmental information output by the environmental information (Continued)

detector, and an output that outputs the environmental level calculated by the calculator.

19 Claims, 14 Drawing Sheets

(51) Int. Cl.
    *A61B 5/16*     (2006.01)
    *A61B 5/00*     (2006.01)
    *G06K 9/00*     (2006.01)

(58) Field of Classification Search
    CPC .... G08B 21/06; G08B 23/00; G06K 9/00624;
                  G06K 8/00624; B60W 40/08; B60W
                  2040/0818; A61M 21/00; G08G 1/16
    USPC ...... 340/575, 576; 128/734, 745; 701/51, 70
    See application file for complete search history.

(56) References Cited

U.S. PATENT DOCUMENTS

| | | | |
|---|---|---|---|
| 8,698,639 B2* | 4/2014 | Fung | B62D 6/007 |
| | | | 340/576 |
| 9,809,115 B2* | 11/2017 | Mader | B60Q 9/008 |
| 9,919,712 B1* | 3/2018 | Doyen | G16H 40/67 |
| 2013/0194099 A1 | 8/2013 | Nagata | |
| 2015/0105976 A1 | 4/2015 | Shikii et al. | |
| 2016/0374606 A1 | 12/2016 | Shikii et al. | |
| 2017/0020432 A1 | 1/2017 | Kusukame et al. | |
| 2017/0102783 A1 | 4/2017 | Shikii et al. | |
| 2017/0150930 A1 | 6/2017 | Shikii et al. | |
| 2019/0299744 A1 | 10/2019 | Kusukame et al. | |

FOREIGN PATENT DOCUMENTS

| | | |
|---|---|---|
| JP | H11-310053 A | 11/1999 |
| JP | 2005-186657 A | 7/2005 |
| JP | 2009-031905 A | 2/2009 |
| JP | 2010-133692 A | 6/2010 |
| JP | 2010-186276 A | 8/2010 |
| JP | 2013-152679 A | 8/2013 |
| JP | 2015-018517 A | 1/2015 |
| JP | 2015-096413 A | 5/2015 |
| JP | 2017-012730 A | 1/2017 |
| JP | 2017-073107 A | 4/2017 |
| JP | 2017-099846 A | 6/2017 |
| JP | 2017-127616 A | 7/2017 |
| JP | 2019-006363 A | 1/2019 |
| JP | 2019-067385 A | 4/2019 |
| KR | 20140147233 A | 12/2014 |
| WO | 2018/105331 A1 | 6/2018 |
| WO | 2019/065749 A1 | 4/2019 |
| WO | 2019/065765 A1 | 4/2019 |

OTHER PUBLICATIONS

International Search Report and Written Opinion dated Jul. 17, 2018 in International Patent Application No. PCT/JP2018/019925; with partial English translation.

* cited by examiner

FIG. 2

| ENVIRONMENTAL LEVEL | 1 | 2 | 3 | 4 | 5 |
|---|---|---|---|---|---|
| HOW LIKELY USER BECOMES SLEEPY | LESS LIKELY TO BECOME SLEEPY | ⋯ | ⋯ | ⋯ | MORE LIKELY TO BECOME SLEEPY |
| CHARACTERISTICS EXAMPLE | · TEMPERATURE: 30°C OR HIGHER<br>· HUMIDITY: 90% OR HIGHER<br>· NOISE: 80 dB OR HIGHER<br>· BRIGHTNESS: 2500 lx OR HIGHER | ⋯ | ⋯ | ⋯ | · TEMPERATURE: 18°C TO 22°C<br>· HUMIDITY: 50–60%<br>· SOUND: 30 dB OR LOWER<br>· BRIGHTNESS: 100 lx OR LOWER |

FIG. 7

| SLEEPINESS LEVEL | 1 | 2 | 3 | 4 | 5 |
|---|---|---|---|---|---|
| DEGREE OF SLEEPINESS | NOT SLEEPY | ... | SLEEPY | ... | VERY SLEEPY |
| CHARACTERISTICS EXAMPLE | ·BLINK AT STABLE CYCLES<br>·LINE OF SIGHT CHANGES RAPIDLY<br>·LINE OF SIGHT CHANGES FREQUENTLY | ·LINE OF SIGHT CHANGES SLOWLY<br>·LIPS BECOME PARTED | ·BLINK SLOWLY<br>·BLINK AT SHORT CYCLES<br>·SECONDARY ACTION OCCURS WHEN BLINKING | ·BLINK AT UNSTABLE CYCLES<br>·YAWN | ·EYELIDS CLOSE<br>·HEAD TILTS FORWARD |

|  | U1 | | U2 | |
| --- | --- | --- | --- | --- |
|  | TEMPERATURE | SLEEPINESS LEVEL | TEMPERATURE | SLEEPINESS LEVEL |
| NO CONTROL | 25 °C | 3 | 25 °C | 2 |
| WITH $CO_2$ CONTROL ON | 25 °C | 2 | 25 °C | 1 |
| INDIVIDUAL TEMPERATURE CONTROL | 23 °C | 1 | 25 °C | 1 |

# SLEEPINESS ESTIMATING DEVICE, WAKEFULNESS INDUCTION CONTROL DEVICE, AND WAKEFULNESS INDUCTION SYSTEM

CROSS-REFERENCE OF RELATED APPLICATIONS

This application is the U.S. National Phase under 35 U.S.C. § 371 of International Patent Application No. PCT/JP2018/019925, filed on May 24, 2018, which in turn claims the benefit of Japanese Application No. 2017-107014, filed on May 30, 2017, the entire disclosures of which Applications are incorporated by reference herein.

TECHNICAL FIELD

The present disclosure relates to a sleepiness estimating device, a wakefulness induction control device, and a wakefulness induction system.

BACKGROUND ART

To date, there is proposed a wakefulness induction control device that induces wakefulness in a person to shake off his/her sleepiness. For example, PTL 1 discloses a device that stimulates a person with heat by controlling the air conditioning to induce wakefulness in that person. In addition, for example, PTL 2 and PTL 3 disclose a device that stimulates a person with a sound by controlling the sound to induce wakefulness in that person. Furthermore, PTL 4 discloses a device that stimulates a person with a scent by controlling equipment that produces the scent to induce wakefulness in that person.

CITATION LIST

Patent Literature

PTL 1: Japanese Unexamined Patent Application Publication No. 2005-186657
PTL 2: Japanese Unexamined Patent Application Publication No. 2009-31905
PTL 3: Japanese Unexamined Patent Application Publication No. 11-109985
PTL 4: Japanese Unexamined Patent Application Publication No. 11-310053

SUMMARY OF THE INVENTION

Technical Problem

To date, the degree of sleepiness of a person is estimated based on an image captured with a camera or the like. In accordance with the degree of sleepiness of the person estimated in this manner, a device that induces wakefulness is actuated in a mode corresponding to the degree of sleepiness of the person.

The present disclosure is directed to providing a sleepiness estimating device and so on that can estimate the degree of sleepiness of a person with higher accuracy.

Solutions to Problem

To address the above issue, a sleepiness estimating device according to one aspect of the present disclosure comprises: an environmental information detector that detects a plurality of conditions of an environment surrounding a person and outputs environmental information indicating the conditions detected of the environment; a calculator that calculates an environmental level indicating a degree of how likely the person becomes sleepy in the environment in accordance with the environmental information output by the environmental information detector; and an output that outputs the environmental level calculated by the calculator.

A wakefulness induction control device according to one aspect of the present disclosure comprises: the sleepiness estimating device described above; and a controller that actuates a wakefulness inducer that induces wakefulness in the person in a mode corresponding to the environmental level.

A wakefulness induction system according to one aspect of the present disclosure comprises: the wakefulness induction control device described above; and the wakefulness inducer described above.

Advantageous Effect of Invention

The sleepiness estimating device and so on according to the present disclosure can estimate the degree of sleepiness of a person with higher accuracy.

BRIEF DESCRIPTION OF DRAWINGS

FIG. 2 illustrates an example of an environmental level corresponding to characteristics examples of environmental information.
FIG. 7 illustrates an example of a person's characteristics corresponding to his/her sleepiness level.

Figure 1:
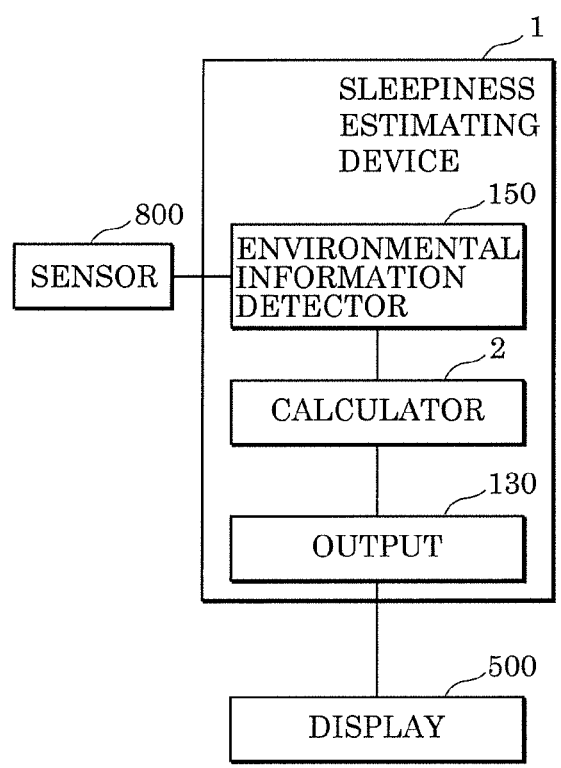
FIG. 1 is a block diagram illustrating a characteristic functional configuration of a sleepiness estimating device according to an embodiment.

DESCRIPTION OF EXEMPLARY
EMBODIMENTS (Overview of the Present Disclosure)

To address the above issue, a sleepiness estimating device according to one aspect of the present disclosure includes an environmental information detector that detects a plurality of conditions of an environment surrounding a person and outputs environmental information indicating the detected conditions of the environment, a calculator that calculates an environmental level indicating the degree of how likely the person becomes sleepy in the environment in accordance with the environmental information output by the environmental information detector, and an output that outputs the environmental level calculated by the calculator.

With this configuration, the sleepiness estimating device can quantitate, as an environmental level, the degree of how likely a person (user) becomes sleepy in a given environment in accordance with a difference in the environment where the person (user) is present. Therefore, the sleepiness estimating device can estimate the degree of sleepiness of the user with higher accuracy. In addition, the sleepiness estimating device, upon the output having been connected to a device such as a display or an amplifier, can notify the user of the quantitated degree of how likely the user becomes sleepy in the environment. Accordingly, as the sleepiness estimating device notifies the user of, as the environmental level, the quantitated degree of how likely the user becomes sleepy in the environment, the user can check the environmental level and take a measure to keep him/her from becoming sleepy, for example.

A wakefulness induction control device according to one aspect of the present disclosure includes the sleepiness estimating device described above and a controller that actuates a wakefulness inducer that induces wakefulness in the person in a mode corresponding to the environmental level.

With this configuration, the controller can actuate a wakefulness inducer in a mode corresponding to the environmental level. Therefore, the wakefulness induction control device can estimate the degree of sleepiness of the user with higher accuracy and induce wakefulness in the user effectively in accordance with the environmental level.

For example, the wakefulness induction control device according to one aspect of the present disclosure may further include a sleepiness detector that detects a sleepiness level indicating the degree of sleepiness of the person, and the controller may actuate the wakefulness inducer when the sleepiness level detected by the sleepiness detector is equal to or higher than a first reference value.

With this configuration, the controller can control the timing of actuating the wakefulness inducer based on the sleepiness level of the user. Therefore, the wakefulness induction control device can induce wakefulness in the user at an effective timing.

For example, when there are a plurality of persons in the environment, the sleepiness detector may detect the sleepiness level of each of the plurality of persons, and the controller may stop the wakefulness inducer when the sleepiness level of each of the plurality of persons is equal to or lower than a second reference value.

With this configuration, the controller can induce wakefulness in the plurality of users under the same environment to a predetermined sleepiness level. In other words, this configuration makes it possible to induce wakefulness in a plurality of users with ease even in an environment where the plurality of users are present.

For example, when the sleepiness level of only one or more of the plurality of persons is higher than the second reference value, the controller may actuate the wakefulness inducer only for the one or more of the plurality of persons.

With this configuration, the controller can execute, for each user, a wakefulness inducing method suitable for each user even when wakefulness cannot be induced in a plurality of users present in the same environment to a predetermined sleepiness level through the same wakefulness inducing method. In other words, this configuration makes it possible to induce wakefulness through a wakefulness inducing method suitable for each user even in an environment where a plurality of users are present.

For example, the wakefulness induction control device according to the present disclosure may further include an acquirer that acquires a control parameter for controlling the wakefulness inducer, and the controller may actuate the wakefulness inducer in a mode corresponding to the control parameter acquired by the acquirer.

For example, the acquirer, upon being connected to a user interface such as a touch panel, acquires, from the user, information on an actuation mode of the wakefulness inducer desired by the user. With this configuration, the controller can actuate the wakefulness inducer in accordance with the information acquired by the acquirer. Therefore, this configuration makes it possible to actuate the wakefulness inducer in a mode desired by the user.

For example, the control parameter may include an actuation duration from when the controller starts actuating the wakefulness inducer to when the controller stops the wakefulness inducer.

With this configuration, the controller automatically stops the wakefulness inducer when the actuation duration included in the control parameter has passed. Therefore, the user of the wakefulness induction control device can be made less likely to become accustomed to the method of inducing wakefulness even when the user has repeatedly used the wakefulness induction control device. In this manner, a decrease in the wakefulness inducing effect can be suppressed by making the user less likely to become accustomed to the wakefulness inducing method.

For example, the control parameter may include a current time, and the controller may change the mode in which the wakefulness inducer is actuated in accordance with the current time indicated by the control parameter.

With this configuration, for example, at a time such as an evening time when the user is presumably likely to become sleepy, an adjustment may be made so as to allow more wakefulness to be induced in the user. Therefore, this configuration can increase the wakefulness inducing effect on the user.

For example, the control parameter may include wakefulness level information indicating the degree of wakefulness for bringing a sleepiness level indicating the degree of sleepiness of the person to a predetermined sleepiness level.

With this configuration, the controller can actuate the wakefulness inducer so as to induce wakefulness to a predetermined sleepiness level desired by the user.

For example, the wakefulness induction control device may be connected to a plurality of wakefulness inducers that differ in the wakefulness inducing method of inducing wakefulness in the person, and the controller may actuate one or more wakefulness inducers of the plurality of wakefulness inducers in the mode corresponding to the environmental level.

With this configuration, the wakefulness induction control device can induce wakefulness in the user through a plurality of different wakefulness inducing methods. Therefore, this configuration makes the user less likely to become accustomed to a wakefulness inducing method and may suppress a decrease in the wakefulness inducing effect.

For example, when the sleepiness level of the person indicating the degree of sleepiness of the person fails to reach or fall below a third reference value for a predetermined duration, the controller may actuate a wakefulness inducer that differs in the wakefulness inducing method from the one or more wakefulness inducers being actuated.

With this configuration, even when one wakefulness inducing method does not succeed in inducing wakefulness in the user, another wakefulness inducing method with a possibility of inducing wakefulness in the user can be executed. Therefore, this configuration suppresses a failure in inducing wakefulness in the user.

A wakefulness induction system according to one aspect of the present disclosure includes the above wakefulness induction control device and the above wakefulness inducer.

With this configuration, the wakefulness induction system according to the present disclosure actuates the wakefulness inducer in accordance with the acquired environmental level. In other words, the wakefulness induction system according to the present disclosure can induce wakefulness in the user through a wakefulness inducing method corresponding to the environment surrounding the user. Therefore, the wakefulness induction system according to the present disclosure can induce wakefulness in the user more effectively than an existing device that induces wakefulness in the user.

Hereinafter, embodiments of the present disclosure will be described with reference to the drawings. The embodiments described below merely illustrate general or specific examples of the present disclosure. Therefore, the numerical values, the constituent elements, the arrangement and the connection modes of the constituent elements, the processes (steps), the order of the processes, and so on illustrated in the following embodiments are examples and are not intended to limit the present disclosure. Accordingly, among the constituent elements in the following embodiments, any constituent element that is not described in an independent claim expressing the broadest concept of the present disclosure will be described as an optional constituent element.

In addition, the drawings are schematic diagrams and do not necessarily provide the exact depictions. Therefore, the scales and so on do not necessarily match among the drawings. In the drawings, substantially identical configurations are given identical reference characters, and duplicate descriptions thereof will be omitted or simplified.

In the following description, such terms as "equal to or higher than a reference value" and "equal to or lower than a reference value" may be used, but these terms are not to be construed in their strict sense. For example, the term "equal to or higher than a reference value" may mean that a given value is higher than the reference value. In addition, when the terms "equal to or higher than a reference value" and "lower than a reference value" are used in a comparative manner, this means that the reference value serves as a discriminating boundary, and the respective terms may mean "higher than a reference value" and "equal to or lower than a reference value."

Embodiments (Sleepiness Estimating Device)
<Configuration>

First, a sleepiness estimating device according to an embodiment will be described with reference to FIGS. 1 to 3.

FIG. 1 is a block diagram illustrating a characteristic functional configuration of a sleepiness estimating device according to an embodiment.

Sleepiness estimating device 1 detects an environment surrounding a person (user) and quantitates the degree of how likely the user becomes sleepy in the detected environment.

As illustrated in FIG. 1, sleepiness estimating device 1 includes environmental information detector 150, calculator 2, and output 130.

Environmental information detector 150 detects the condition of an environment surrounding the user and outputs environmental information indicating the detected condition of the environment. Specifically, environmental information detector 150 includes an interface to be connected to sensor 800. Environmental information detector 150 detects the condition of the environment sensed by sensor 800 and outputs the environmental information indicating the detected condition of the environment to calculator 2. The environmental information indicates the condition of the environment surrounding the user and is information on, for example, the temperature, the humidity, the $CO_2$ concentration, the illuminance, the sound, the scent, or the like. The environmental information may further include spatial information indicating the space where the user is. Here, the spatial information indicates that the user is in a vehicle, in an office, at school, or the like, for example.

Calculator 2 calculates an environmental level based on the environmental information detected by environmental information detector 150.

The environmental level is a quantitated numerical value indicating the degree of how likely the user becomes sleepy in the environment surrounding the user. For example, when a certain environment is an environment where the user is more likely to become sleepy, calculator 2 calculates the environmental level to be higher. In addition, for example, when a certain environment is an environment where the user is less likely to become sleepy, calculator 2 calculates the environmental level to be lower. Specifically, when the environment surrounding the user is dark, this environment is considered to be an environment where the user is more likely to become sleepy. In such a case, calculator 2 acquires information indicating the brightness of the environment output by environmental information detector 150 and calculates, based on the acquired information, the environmental level of this environment to be higher through a predetermined calculation method. In another specific example, when the environment surrounding the person is highly noisy, this environment is considered to be an environment where the user is less likely to become sleepy. In such a case, calculator 2 calculates the environmental level of this environment to be lower.

Calculator 2 is implemented, for example, with a central processing unit (CPU) and a control program stored in a storage communicably connected to sleepiness estimating device 1. Examples of the storage include a read only memory (ROM), a random access memory (RAM), a hard disk drive (HDD), and a solid state drive (SSD).

FIG. 2 illustrates an example of the environmental level corresponding to characteristics examples of the environmental information. Environmental information detector 150 detects one or more of the characteristics examples indicated in the table in FIG. 2 as the condition of the environment and outputs, to calculator 2, the condition of the detected environment as the environmental information.

As illustrated in FIG. 2, for example, when the temperature in the environment is 18-22° C., the humidity is 50-60%, the sound is 30 dB (decibel) or lower, and the brightness is 100 lx (lux) or lower, this environment is considered to be an environment where the user is more likely to become sleepy. In such a case, the environmental level is high, and calculator 2 calculates the environmental level to be 5, for example. Meanwhile, for example, when the temperature in the environment is 30° C., the humidity is 90%, the sound is 80 dB or higher, and the brightness is 2500 lx or higher, this environment is considered to be an environment where the user is less likely to become sleepy. In such a case, the environmental level is low, and calculator 2 calculates the environmental level to be 1, for example.

In this manner, calculator 2 calculates the environmental level of the environment surrounding the user based on the environmental information output by environmental information detector 150. The relationship between the environmental level and the characteristics examples of the environment illustrated in FIG. 2 is merely an example, and this is not a limiting example. For example, the environmental level may be classified into six or more levels or into four or less levels. The method of calculating the environmental level may be set as desired, and there is no particular limitation thereon. Calculator 2 may determine the environmental level through a calculation with a predetermined weight given to each piece of the environmental information, such as the temperature, the brightness, or the sound. In addition, as the user is more likely to become sleepy, the numerical value of the environmental level may be set lower. In the following description, that the environmental level is low means that the user is less likely to become sleepy.

Output 130 is an interface for outputting information to notify the user of the environmental level calculated by calculator 2. Output 130 is connected, for example, to display 500, which is a display device such as a display, and outputs, to display 500, display information, including characters and/or pictures, representing the environmental level calculated by calculator 2. For example, display 500 displays the acquired display information in the form of an image. Examples of display 500 include a monitor device constituted by a liquid crystal panel, an organic EL panel, or the like. An information terminal having a display, such as a television set, a smartphone, or a tablet terminal, may also be used as display 500.

Figure 3:
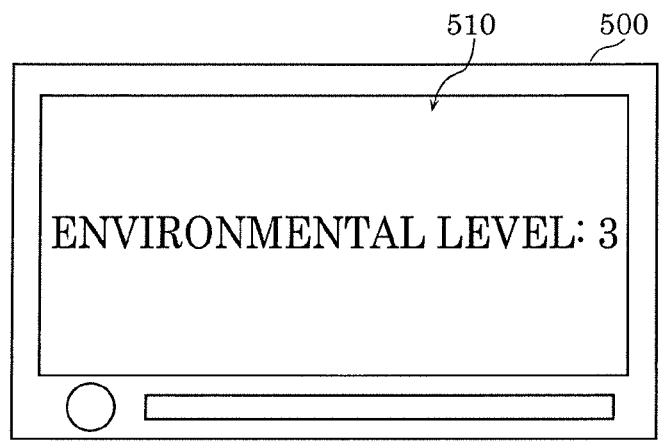
FIG. 3 illustrates an example of an output result for a sleepiness estimating device according to an embodiment to notify a user of an environmental level.

FIG. 3 illustrates an example of an output result for sleepiness estimating device 1 according to the embodiment to notify the user of the environmental level.

Calculator 2 causes output 130 to output, to display 500, environmental level information indicating the calculated environmental level. Display 500 displays, for example, image 510 illustrated in FIG. 3. This configuration makes it possible to present, to the user, whether the environment surrounding the user is an environment where the user is more likely to become sleepy. Thus, the user can easily recognize how likely the user becomes sleepy in that environment. This makes it possible to prompt the user to so improve the environment as to make the user less likely to become sleepy, for example.

Output 130 may be connected to a speaker or the like and output audio information indicating the environmental level calculated by calculator 2, for example.

<Operation>

Now, an operation of sleepiness estimating device 1 according to the embodiment will be described with reference to FIG. 4.

Figure 4:
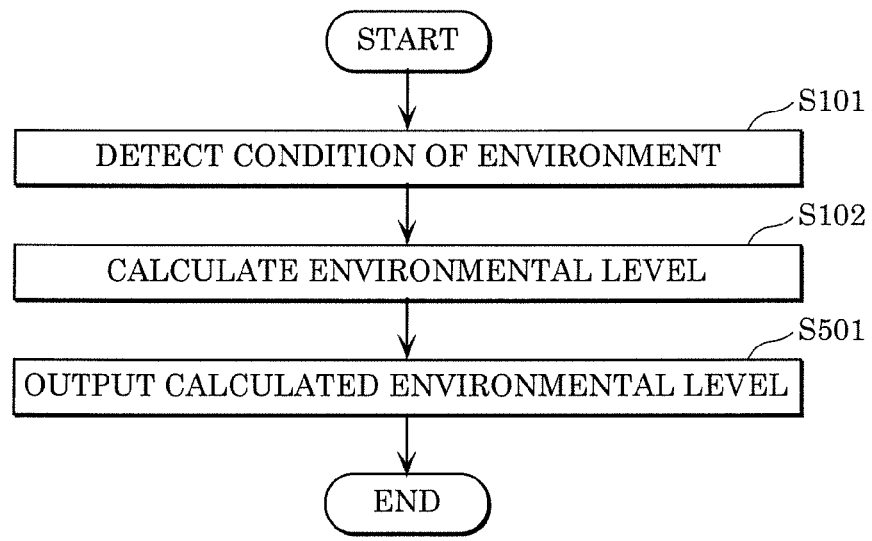
FIG. 4 is a flowchart through which a sleepiness estimating device according to an embodiment outputs the degree of how likely a person becomes sleepy in a surrounding environment.

FIG. 4 is a flowchart illustrating a procedure through which sleepiness estimating device 1 according to the embodiment calculates the environmental level of the environment surrounding the user.

Environmental information detector 150 detects the condition of the environment surrounding the user (step S101). Environmental information detector 150 outputs, to calculator 2, the condition, such as the brightness, the sound volume, or the temperature, of the environment surrounding the user and sensed by sensor 800 as the environmental information.

Then, calculator 2 calculates the environmental level based on the environmental information output by environmental information detector 150 (step S102).

Then, calculator 2 outputs the environmental level information indicating the calculated environmental level to output 130 (step S501). Display 500 acquires the environmental level information output by output 130 and displays image 510 illustrated in FIG. 3, for example.

In this manner, sleepiness estimating device 1 includes environmental information detector 150 that detects the environment surrounding the user, calculator 2 that quantitatively calculates the degree of how likely the user becomes sleepy in the environment detected by environmental information detector 150, and output 130 that outputs the result calculated by calculator 2. With this configuration, sleepiness estimating device 1 can inform the user of the environmental level obtained by quantitating the degree of how likely the user becomes sleepy in the environment surrounding the user. Accordingly, sleepiness estimating device 1 can estimate the degree of sleepiness of the user with higher accuracy and inform the user. The user can then check the environmental level and take a measure to keep him/her from becoming sleepy, for example.

[Wakefulness Induction Control Device and Wakefulness Induction System]

<Configuration>

Now, a configuration of a wakefulness induction control device and a wakefulness induction system according to the embodiment will be described with reference to FIGS. 5 and 6.

Figure 5:
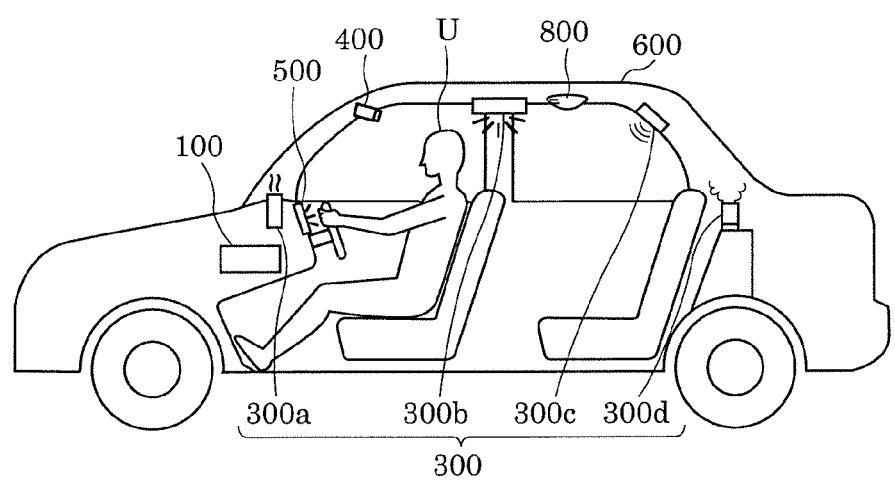
FIG. 5 is an illustration for describing an example of a system including a wakefulness induction control device according to an embodiment.

FIG. 5 is an illustration for describing an example of a system including the wakefulness induction control device according to the embodiment. FIG. 6 is a block diagram illustrating a characteristic functional configuration of the wakefulness induction control device according to the embodiment.

Wakefulness induction control device 100 is provided, for example, in vehicle 600 illustrated in FIG. 5 and induces wakefulness in user U, such as a driver of vehicle 600.

Figure 6:
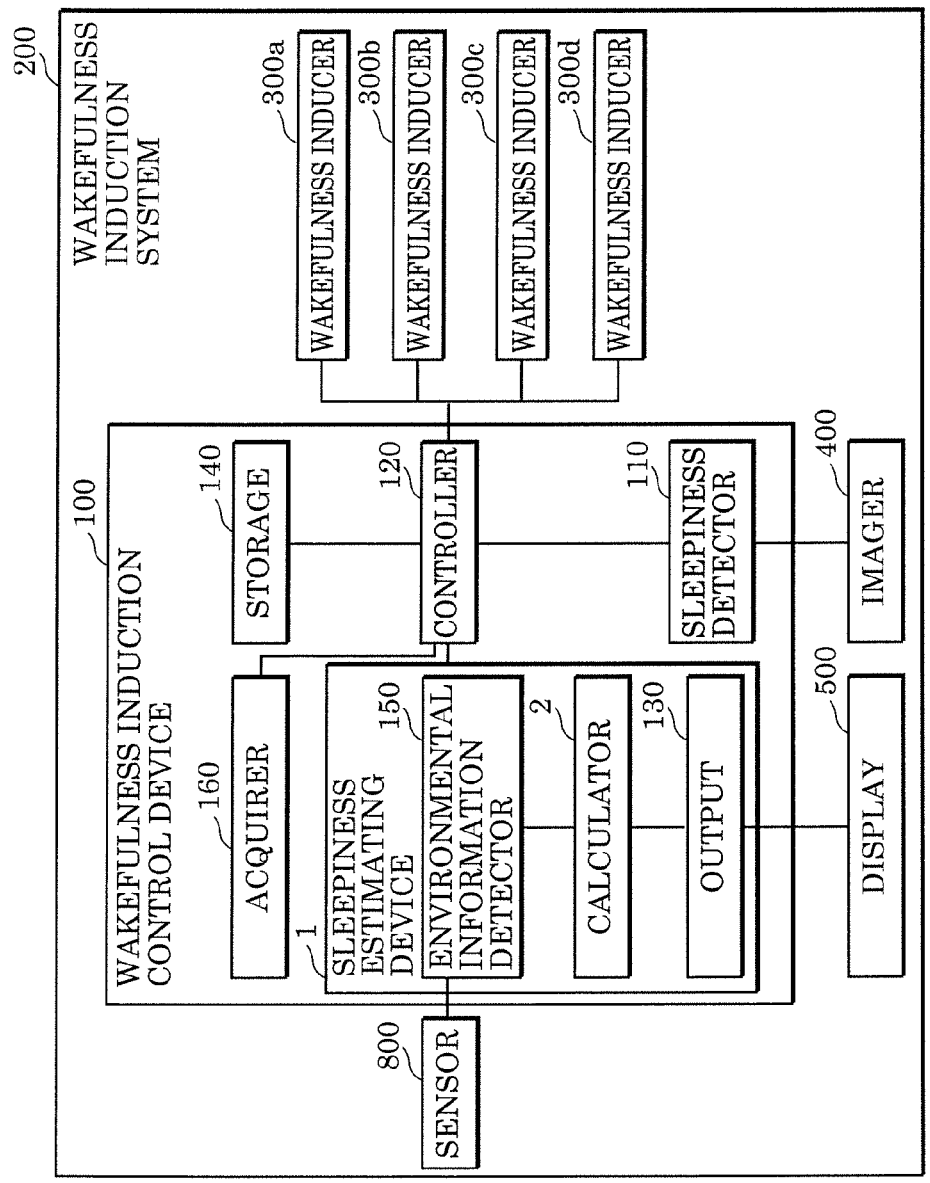
FIG. 6 is a block diagram illustrating a characteristic functional configuration of a wakefulness induction control device according to an embodiment.

As illustrated in FIG. 6, wakefulness induction control device 100 includes sleepiness estimating device 1, sleepiness detector 110, controller 120, storage 140, and acquirer 160.

Sleepiness detector 110 detects the sleepiness level indicating the degree of sleepiness of user U. To rephrase, sleepiness detector 110 detects the degree of wakefulness of user U. For example, sleepiness detector 110 includes an interface for acquiring a moving image that includes user U captured by imager 400 connected to sleepiness detector 110 and detects the sleepiness level of user U based on this moving image. Sleepiness detector 110 outputs the detected sleepiness level of user U to controller 120. There is no particular limitation on the method of detecting the sleepiness level of user U, and the sleepiness level can be detected, for example, based on moving image information of the face of user U.

FIG. 7 illustrates an example of characteristics of user U corresponding to his/her sleepiness level.

As illustrated in FIG. 7, for example, when user U blinks at stable cycles, the sleepiness level is low and is determined to be 1, for example. When user U blinks slowly and frequently at short cycles, the sleepiness level is high and is determined to be 3, for example. In other words, user U is determined not to be sleepy when user U blinks at stable cycles and is determined to be sleepy when user U blinks slowly and frequently. In this manner, sleepiness detector 110 detects the sleepiness level of user U by analyzing a moving image that includes user U acquired by imager 400. The relationship among the sleepiness level, the degree of sleepiness, and the characteristics examples illustrated in FIG. 7 is merely an example, and this is not a limiting example. For example, the sleepiness level may be classified into six or more levels or into four or less levels. The reference based on which the sleepiness level is determined may be set as desired, and there is no particular limitation thereon. In addition, as the degree of sleepiness of user U is higher, the numerical value of the sleepiness level may be set lower. In the following description, that the sleepiness level is low means that the degree of sleepiness of the user is low.

Examples of imager 400 include a camera including a complementary metal oxide semiconductor (CMOS) image sensor and a camera including a charge coupled device (CCD) image sensor.

Referring back to FIG. 6, controller 120 actuates (i.e., starts actuating) one or more of wakefulness inducers 300a to 300d that each induce wakefulness in user U in a mode corresponding to the environmental level calculated by calculator 2. For example, when the sleepiness level detected by sleepiness detector 110 is equal to or higher than a first reference value, controller 120 actuates one or more of wakefulness inducers 300a to 300d that each induce wakefulness in user U in a mode corresponding to the environmental level calculated by calculator 2. In the following description, wakefulness inducers 300a to 300d may be collectively referred to as wakefulness inducer(s) 300. Wakefulness induction control device 100 is connected to one or more wakefulness inducers 300 via a wire (not illustrated) or the like. For example, when the environmental level is high, user U is an environment where user U is more likely to become sleepy, and thus controller 120 actuates all wakefulness inducers 300 connected to wakefulness induction control device 100 to induce wakefulness in user U. Meanwhile, for example, when the environmental level is low, user U is an environment where user U is less likely to become sleepy, and thus controller 120 actuates one of the plurality of wakefulness inducers 300 connected to wakefulness induction control device 100 to induce wakefulness in user U.

Sleepiness detector 110 and controller 120 are implemented, for example, with a CPU and a control program stored in storage 140. Sleepiness detector 110, controller 120, and calculator 2 may be implemented with a single CPU or may each be implemented with a separate CPU.

Wakefulness inducers 300 are devices used to lower the sleepiness level of user U. Examples of wakefulness inducers 300 include an acoustic device that emits a sound, an emission device that emits light, an aroma generator that produces a scent, and an air conditioner that controls the air conditioning, such as the temperature, the humidity, or the $CO_2$ concentration. In other words, wakefulness inducers 300 are devices that induce wakefulness by stimulating user U with a sound, light, heat, or the like or devices that lower the humidity, the $CO_2$ concentration, or the like to improve the environment causing the sleepiness in user U.

It suffices that the first reference value be preset, and there is no particular limitation on the sleepiness level. For example, the first reference value indicating that the sleepiness level is 3 may be prestored in storage 140. For example, controller 120 actuates wakefulness inducer 300 when the sleepiness level detected by sleepiness detector 110 meets the first reference value.

Controller 120 stops wakefulness inducer 300 when the sleepiness level of user U has fallen to a second reference value, for example. Controller 120 may stop wakefulness inducer 300 when a predetermined duration has passed after actuation of wakefulness inducer 300. Like the first reference value, it suffices that the second reference value be preset as desired, and there is no particular limitation on the sleepiness level. For example, the second reference value indicating that the sleepiness level is 1 may be prestored in storage 140. In addition, any desired preset duration may be used as the predetermined duration, and there is no particular limitation on the predetermined duration. For example, the predetermined duration is preset to 5 minutes, 10 minutes, 15 minutes, or the like. Wakefulness induction control device 100 may include a time tracker (not illustrated), such as a real time clock (RTC), for measuring the duration.

In one conceivable case, there may be a plurality of users in a given environment. In this case, sleepiness detector 110 may detect the sleepiness level of each of the plurality of users. Controller 120 may stop wakefulness inducer 300 when the sleepiness level of each of the plurality of users has reached or fallen below the second reference value. Here, controller 120 may actuate wakefulness inducer 300 only for one or more of the users when the sleepiness levels of only the one or more of the plurality of users are higher than the second reference value.

Acquirer 160 is an interface that acquires a control parameter for controlling wakefulness inducer 300. For example, acquirer 160 is connected to a user interface, such as a touch panel, and acquires information of an operation on the user interface by user U. Specifically, acquirer 160 acquires a control parameter from user U.

The control parameter includes, for example, an actuation duration from when controller 120 starts actuating wakefulness inducer 300 to when controller 120 stops wakefulness inducer 300.

In addition, the control parameter includes, for example, a current time. Controller 120 changes the mode in which wakefulness inducer 300 is actuated in accordance with the current time indicated by the control parameter.

The control parameter may further include wakefulness level information indicating the degree of wakefulness for bringing the sleepiness level that indicates the degree of sleepiness of user U to a predetermined sleepiness level. For example, the wakefulness level information includes stop reference information indicating the sleepiness level of user U at which wakefulness inducer 300 is to be stopped. In other words, the stop reference information corresponds to the second reference value described above. For example, in a case in which the second reference value is preset as desired, controller 120 changes the method of controlling wakefulness inducer 300 to stop wakefulness inducer 300 when, upon the stop reference information having been acquired, user U has reached the sleepiness level indicated by the acquired stop reference information.

In addition, when controller 120 has acquired the wakefulness level information, controller 120 may select wakefulness inducer 300 to be actuated in accordance with the acquired wakefulness level information. For example, when user U has set the degree of wakefulness to the highest (e.g., when the sleepiness level has been set to 1), controller 120 actuates all wakefulness inducers 300 connected to wakefulness induction control device 100. Meanwhile, when user U has set the degree of wakefulness to a medium (e.g., when the sleepiness level has been set to 3), controller 120 successively actuates wakefulness inducers 300 in order of reduced power consumption. In this case, with regard to the order of priority of the wakefulness inducing method of wakefulness inducer 300 to be actuated, controller 120 may select wakefulness inducer 300 to be actuated in order of the illumination, the scent, the air conditioning (temperature and humidity control), and the ventilation ($CO_2$ control), for example.

The control parameter may further include a mode setting in which controller 120 actuates wakefulness inducer 300. This mode may include, for example, an energy saving mode in which controller 120 actuates, as wakefulness inducer 300, not the air conditioner or a ventilation fan with higher power consumption but one that induces wakefulness in user U with illumination or a scent. In addition, when the energy saving mode has been acquired, controller 120 may actuate, for example, an air conditioner that controls the temperature and the humidity as wakefulness inducer 300. In this case, controller 120 may so actuate wakefulness inducer 300 as not to bring the temperature lower than the temperature to be held when the energy saving mode is not acquired. In addition, when the energy saving mode has been acquired, controller 120 may actuate a ventilation fan that ventilates the air as wakefulness inducer 300. In this case, controller 120 may so actuate wakefulness inducer 300 as to keep the volume of the air moved by the ventilation fan less than the volume of air to be moved when the energy saving mode is not acquired. The mode in which controller 120 actuates wakefulness inducer 300 may include a wakefulness priority mode in which controller 120 actuates all wakefulness inducers 300 connected to wakefulness induction control device 100. The mode in which controller 120 actuates wakefulness inducer 300 may further include a good sleep mode in which controller 120 actuates wakefulness inducer 300 that, with no change in the color temperature of the illumination light emitted by a light emitting diode (LED) illumination serving as an example of wakefulness inducer 300, executes a different wakefulness inducing method. Alternatively, in the good sleep mode, controller 120 may control wakefulness inducer 300 so as not to make the color temperature of the illumination light emitted from wakefulness inducer 300 too blue (i.e., set the color temperature lower than the color temperature to be held when the good sleep mode is not acquired).

In this manner, controller 120 actuates or stops wakefulness inducer 300 in a mode corresponding to a control parameter acquired by acquirer 160.

When wakefulness induction control device 100 includes a plurality of wakefulness inducers 300 that differ in the wakefulness inducing method, controller 120 actuates each wakefulness inducer 300 of one or more wakefulness inducers 300 of the plurality of wakefulness inducers 300. In this case, controller 120 may actuate each wakefulness inducer 300 of the plurality of wakefulness inducers 300 sequentially or may randomly select and actuate wakefulness inducer 300. In addition, controller 120 may actuate one or more wakefulness inducers 300 different from one or more wakefulness inducers 300 actuated in a previous instance. In addition, for example, controller 120 may select one or more wakefulness inducers 300 from the plurality of wakefulness inducers 300 in accordance with the current time and actuate selected one or more wakefulness inducers 300. In addition, for example, controller 120 may select one or more wakefulness inducers 300 from the plurality of wakefulness inducers 300 in accordance with the season and actuate selected one or more wakefulness inducers 300. Wakefulness induction control device 100 may further include storage 140 that stores, for each wakefulness inducer 300, the amount of decrease (the amount of change) in the sleepiness level of user U with respect to the predetermined duration. In this case, controller 120 may actuate one or more wakefulness inducers 300 including wakefulness inducer 300 of which the amount of decrease in the sleepiness level of user U with respect to the predetermined duration stored in storage 140 is largest. To rephrase, controller 120 may actuate one or more wakefulness inducers 300 including wakefulness inducer 300 of which the amount of change in the sleepiness level of user U in the direction of increasing wakefulness of user U with respect to the predetermined duration stored in storage 140 is largest.

When the sleepiness level of user U fails to reach or fall below a third reference value for a predetermined duration, controller 120 may actuate wakefulness inducer 300 different from one or more wakefulness inducers 300 being actuated. The third reference value is set, for example, to a value that is smaller than the first reference value but greater than the second reference value. In a conceivable case, for example, wakefulness may not be induced successfully in user U depending on the physical condition or the like of user U. In this case, if the sleepiness level of user U has failed to reach or fall below the third reference value when the predetermined duration has passed after wakefulness inducer 300 has been actuated, controller 120 actuates wakefulness inducer 300 different from wakefulness inducer 300 being actuated to induce wakefulness in user U. In this case, controller 120 may stop wakefulness inducer 300 being actuated or may allow wakefulness inducer 300 to continue being actuated. The third reference value may be set to a value equal to the first reference value or the second reference value.

Storage 140 is a storage device that stores a control program to be executed by sleepiness detector 110, controller 120, and calculator 2. Storage 140 may be, for example, a ROM, a RAM, an HDD, an SSD, or the like.

The configuration of wakefulness induction control device 100 illustrated in FIG. 6 is an illustrative example for describing the present disclosure in concrete terms, and wakefulness induction control device 100 according to the present disclosure does not need to include all the components illustrated in FIG. 6. To rephrase, it suffices that wakefulness induction control device 100 according to the present disclosure have a configuration that can achieve the effect of the present disclosure.

Figure 8A:
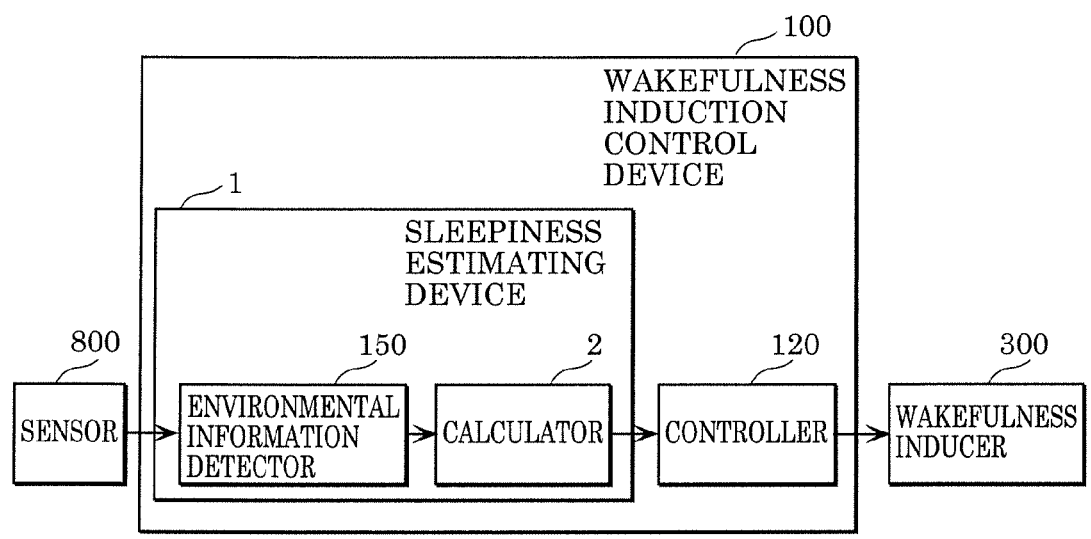
FIG. 8A is a block diagram illustrating an example of a configuration of a wakefulness induction control device according to Variation 1 of an embodiment.

For example, FIG. 8A is a block diagram illustrating an example of a configuration of wakefulness induction control device 100 according to Variation 1 of an embodiment of the present disclosure.

As illustrated in FIG. 8A, wakefulness induction control device 100 includes sleepiness estimating device 1 and controller 120. The processors perform the same processes as those of the processors given the same reference characters indicated in FIG. 6, and thus descriptions thereof will be omitted here.

Figure 8B:
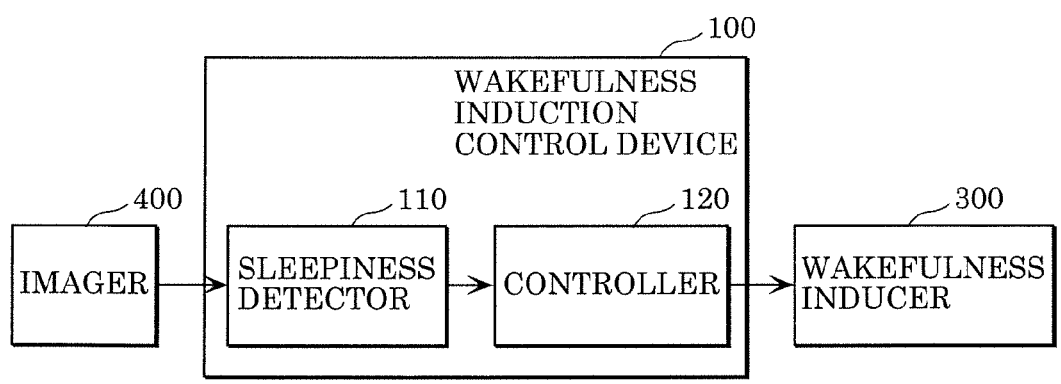
FIG. 8B is a block diagram illustrating an example of a configuration of a wakefulness induction control device according to Variation 1 of an embodiment.

In sleepiness estimating device 1 illustrated in FIG. 8A, calculator 2 calculates the sleepiness level from the condition of the environment detected by environmental information detector 150 based on the output detected by sensor 800, but calculation of the sleepiness level is not limited to this mode. For example, sleepiness detector 110 may calculate the sleepiness level based on the condition of a person (not illustrated). Specifically, as illustrated in FIG. 8B, sleepiness detector 110 may calculate the sleepiness level of the person based on the condition of blinking of user U captured by imager 400, for example. With this configuration, sleepiness detector 110 can estimate (detect) the sleepiness level of user U with higher accuracy.

With this configuration as well, wakefulness induction control device 100 can execute an operation according to the flowchart illustrated in FIG. 9, which will be described later, for example.

<Operation>

Now, an operation of wakefulness induction control device 100 and wakefulness induction system 200 according to an embodiment will be described with reference to FIGS. 9 to 17B. In the following description, as the reference based on which the sleepiness level is determined, the relationship among the sleepiness level, the degree of sleepiness, and the characteristics examples illustrated in FIG. 7 is prestored in storage 140. In addition, an algorithm for weighting the environmental level illustrated in FIG. 2 with respect to the environmental information and for calculating the environmental level from the weighting is prestored in storage 140. In the following description, the first reference value indicating that the sleepiness level is 3 is set. In addition, in the following description, the second reference value indicating that the sleepiness level is 1 is set. Furthermore, in the following description, the third reference value indicating that the sleepiness level is 2 is set.

Figure 9:
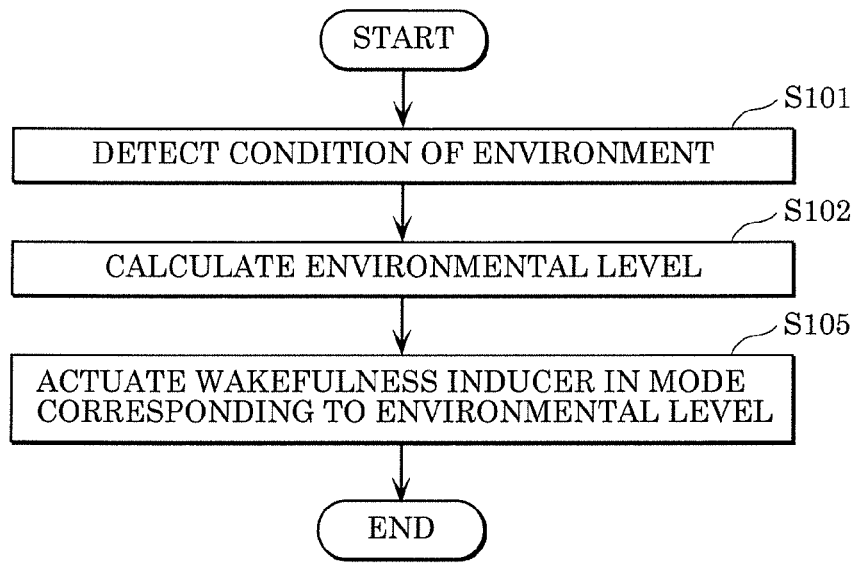
FIG. 9 is a flowchart illustrating a procedure through which a wakefulness induction control device according to an embodiment actuates a wakefulness inducer in a mode corresponding to an environmental level.

FIG. 9 is a flowchart illustrating a procedure through which wakefulness induction control device 100 according to the embodiment actuates wakefulness inducer 300 in a mode corresponding to an environmental level.

Environmental information detector 150 detects the condition of the environment surrounding user U (step S101). Environmental information detector 150 outputs, as the environmental information, the condition, such as the brightness, the sound volume, or the temperature, of the environment surrounding user U detected by sensor 800 to controller 120.

Then, calculator 2 calculates the environmental level based on the environmental information output by environmental information detector 150 (step S102).

Then, controller 120 actuates wakefulness inducer 300 in a mode corresponding to the environmental level calculated by calculator 2 (step S105).

In this manner, controller 120 actuates wakefulness inducer 300 in a mode corresponding to the environmental level calculated by calculator 2.

With this configuration, wakefulness induction control device 100 according to the present disclosure can induce wakefulness in user U through a wakefulness inducing method corresponding to the environment surrounding user U. Therefore, wakefulness induction control device 100 according to the present disclosure can induce wakefulness in user U more effectively than an existing device that induces wakefulness in user U.

Figure 10:
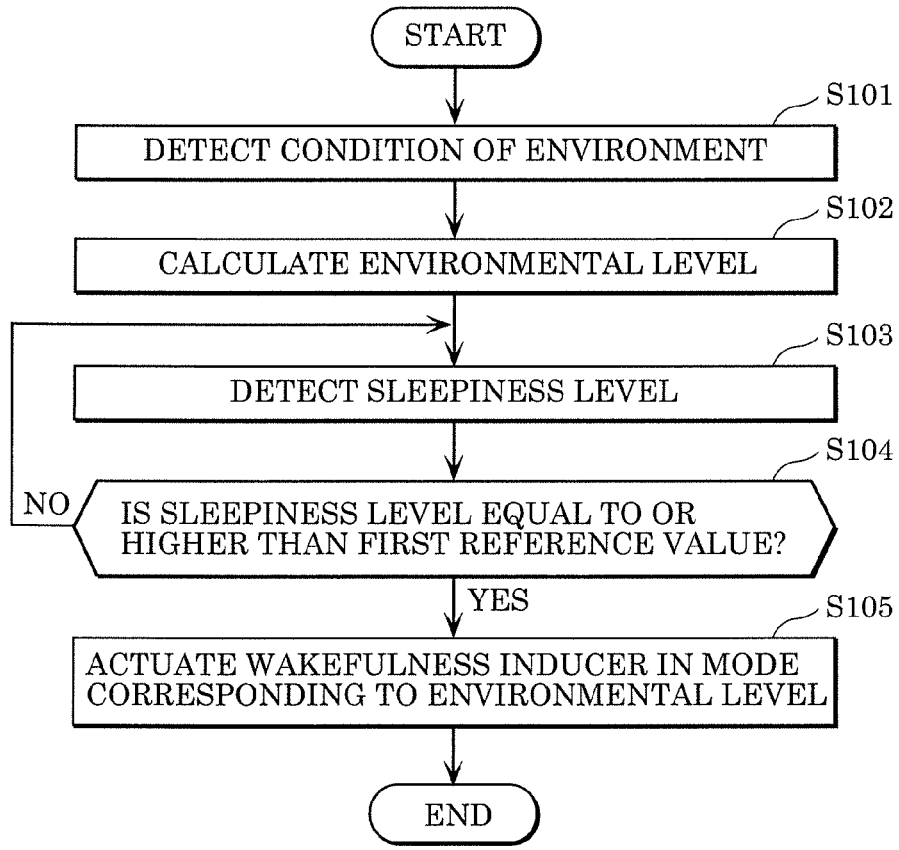
FIG. 10 is a flowchart illustrating a procedure through which a wakefulness induction control device according to an embodiment actuates a wakefulness inducer in a mode corresponding to an environmental level and a sleepiness level.

FIG. 10 is a flowchart illustrating a procedure through which wakefulness induction control device 100 according to the embodiment actuates wakefulness inducer 300 in a mode corresponding to an environmental level and a sleepiness level.

Environmental information detector 150 detects the condition of the environment surrounding user U (step S101). Environmental information detector 150 outputs, as the environmental information, the condition, such as the brightness, the sound volume, or the temperature, of the environment surrounding user U detected by sensor 800 to controller 120.

Then, calculator 2 calculates the environmental level based on the environmental information output by environmental information detector 150 (step S102).

Then, sleepiness detector 110 detects the sleepiness level of user U (step S103). For example, sleepiness detector 110 detects the sleepiness level of user U by acquiring a moving image captured by imager 400 and analyzing the acquired moving image.

Then, controller 120 determines whether the sleepiness level detected by sleepiness detector 110 is equal to or higher than the first reference value (step S104). When controller 120 has determined that the sleepiness level is neither equal to nor higher than the first reference value (NO in step S104), sleepiness detector 110 and controller 120 continue to execute the operations in step S103 and step S104.

Meanwhile, when controller 120 has determined that the sleepiness level is equal to or higher than the first reference value (YES in step S104), controller 120 actuates wakefulness inducer 300 in a mode corresponding to the environmental level calculated by calculator 2 (step S105).

Figure 11:
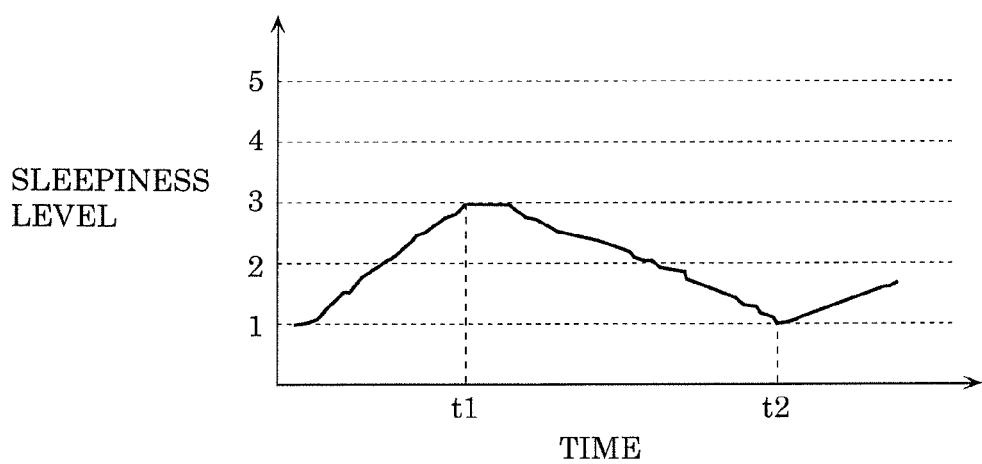
FIG. 11 illustrates an example of a change in the sleepiness level with respect to the time obtained when a wakefulness induction control device according to an embodiment is used.

FIG. 11 illustrates an example of a change in the sleepiness level with respect to the time obtained when wakefulness induction control device 100 according to the embodiment is used. FIG. 11 is a graph illustrating an example of a change in the sleepiness level of user U obtained when controller 120 has caused wakefulness inducer 300 to operate in accordance with the flowchart illustrated in FIG. 10. In the graph illustrated in FIG. 11, the horizontal axis represents the time, and the vertical axis represents the sleepiness level.

As illustrated in FIG. 11, the sleepiness level of user U rises along with the passage of time. At time t1, the sleepiness level of user U reaches 3. At this point, controller 120 actuates wakefulness inducer 300 (step S105 indicated in FIG. 10). As more time passes, the sleepiness level of user U gradually decreases. At time t2, controller 120 stops wakefulness inducer 300 since the sleepiness level of user U has reached the second reference value.

As described above, wakefulness induction control device 100 includes environmental information detector 150 that detects the condition of the environment surrounding user U and outputs the environmental information indicating the detected condition of the environment, sleepiness detector 110 that detects the sleepiness level indicating the degree of sleepiness of user U, and controller 120. Calculator 2 calculates the environmental level indicating the degree of how likely user U becomes sleepy in the environment in accordance with the environmental information output by environmental information detector 150. In addition, when the sleepiness level detected by sleepiness detector 110 is equal to or higher than the first reference value, controller 120 actuates wakefulness inducer 300 in a mode corresponding to the environmental level calculated by calculator 2.

With this configuration, controller 120 actuates wakefulness inducer 300 in accordance with the environmental level calculated by calculator 2. In other words, wakefulness induction control device 100 according to the present disclosure can induce wakefulness in user U through a wakefulness inducing method corresponding to the environment surrounding user U. Therefore, wakefulness induction control device 100 according to the present disclosure can induce wakefulness in user U more effectively than an existing device that induces wakefulness in user U.

The present disclosure may be configured as a system that includes wakefulness induction control device 100 and one or more wakefulness inducers 300. To rephrase, wakefulness induction system 200 according to the present disclosure includes wakefulness induction control device 100 and wakefulness inducer(s) 300.

With this configuration, wakefulness induction system 200 according to the present disclosure actuates wakefulness inducer 300 in accordance with the calculated environmental level. In other words, wakefulness induction system 200 according to the present disclosure can induce wakefulness in user U through a wakefulness inducing method corresponding to the environment surrounding user U. Therefore, wakefulness induction system 200 according to the present disclosure can induce wakefulness in user U more effectively than an existing device that induces wakefulness in user U.

Controller 120 may actuate wakefulness inducer 300 in a mode corresponding to a control parameter acquired by acquirer 160.

Figure 12:
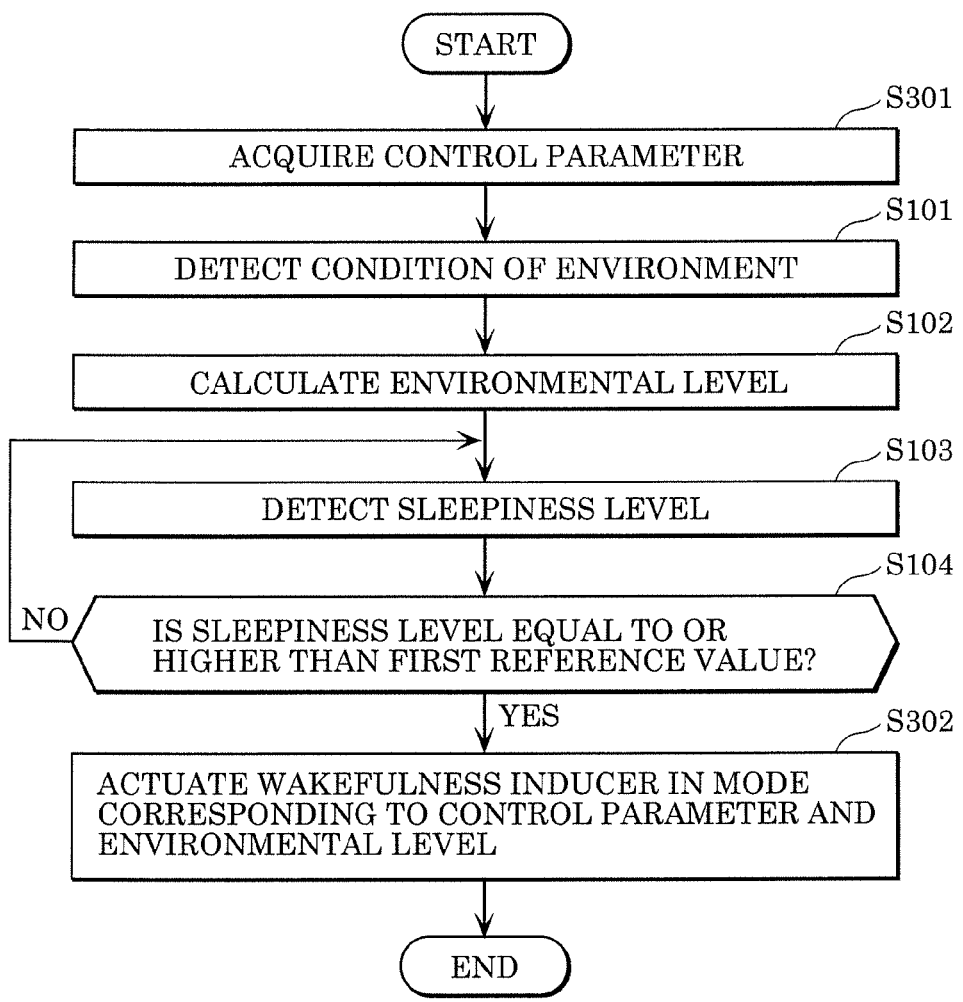
FIG. 12 is a flowchart illustrating a procedure through which a wakefulness induction control device according to an embodiment actuates a wakefulness inducer in accordance with a control parameter.

FIG. 12 is a flowchart illustrating a procedure through which wakefulness induction control device 100 according to the embodiment actuates wakefulness inducer 300 in accordance with a control parameter.

Acquirer 160 acquires a control parameter (step S301). For example, acquirer 160 is a communication interface and acquires a control parameter from a smartphone, a personal computer, or the like operated by user U and communicably connected to acquirer 160 with a cable or wirelessly. Wakefulness induction system 200 may include an operator, such as a touch panel, to be operated by the user. In this case, this operator is communicably connected to acquirer 160 with a cable or wirelessly. User U inputs a control parameter by operating the operator. Acquirer 160 acquires the control parameter input through the operator.

Then, environmental information detector 150, calculator 2, sleepiness detector 110, and controller 120 execute operations similar to those in step S101 to step S104 illustrated in FIG. 10.

Then, when controller 120 has determined that the sleepiness level is equal to or higher than the first reference value (YES in step S104), controller 120 actuates the wakefulness inducer in a mode corresponding to the control parameter acquired by acquirer 160 and the environmental level calculated by calculator 2 (step S302).

For example, when the control parameter includes the actuation duration from when controller 120 starts actuating wakefulness inducer 300 to when controller 120 stops wakefulness inducer 300, controller 120 actuates and stops wakefulness inducer 300 in accordance with this actuation duration. In addition, for example, when the control parameter includes the current time, controller 120 changes the mode in which wakefulness inducer 300 is actuated in accordance with the current time indicated by the control parameter.

For example, if the current time indicates an evening time when user U is more likely to become sleepy, controller 120 may actuate wakefulness inducer 300 so as to further induce wakefulness in user U. If wakefulness inducer 300 is a device that emits a sound, controller 120 may actuate wakefulness inducer 300 with a larger sound volume than the sound volume to be held when the current time indicates some other time. When wakefulness inducer 300 includes a plurality of wakefulness inducers 300, controller 120 may actuate all wakefulness inducers 300. In addition, for example, when the current time indicates a night time, controller 120 may actuate wakefulness inducer 300 so as not to induce too much wakefulness in user U. If wakefulness inducer 300 is a device that emits light, controller 120 may actuate wakefulness inducer 300 with a smaller amount of light than the amount of light to be held when the current time indicates some other time.

The control parameter may further include wakefulness level information indicating the degree of wakefulness for bringing the sleepiness level that indicates the degree of sleepiness of user U to a predetermined sleepiness level. When the wakefulness level information includes the stop reference information indicating the sleepiness level of user U at which wakefulness inducer 300 is to be stopped, controller 120 changes the method of controlling wakefulness inducer 300 to stop wakefulness inducer 300 when the user U has reached the sleepiness level indicated by the stop reference information even if the second reference value is preset as desired.

In addition, when controller 120 has acquired the wakefulness level information as the control parameter, controller 120 may select wakefulness inducer 300 to be actuated in accordance with the acquired wakefulness level information.

The control parameter may further include the mode setting in which controller 120 actuates wakefulness inducer 300. Examples of this mode include the energy saving mode, the wakefulness priority mode, and the good sleep mode, as described above.

When wakefulness induction control device 100 is connected to a plurality of wakefulness inducers 300 that differ in the wakefulness inducing method of inducing wakefulness in user U, the control parameter may include an instruction on the wakefulness inducing method. When acquirer 160 has acquired the instruction on the wakefulness inducing method, controller 120 actuates wakefulness inducer 300 that can execute the wakefulness inducing method indicated by this instruction.

In this manner, wakefulness induction control device 100 may include acquirer 160 that acquires the control parameter for controlling wakefulness inducer 300. Controller 120 may actuate wakefulness inducer 300 in a mode corresponding to the control parameter acquired by acquirer 160. For example, acquirer 160, upon being connected to a user interface such as a touch panel, may acquire, from user U, information on the actuation mode of wakefulness inducer 300 desired by user U.

With this configuration, controller 120 can actuate wakefulness inducer 300 in a mode corresponding to the information acquired by acquirer 160. Therefore, this configuration makes it possible to actuate wakefulness inducer 300 in a mode desired by user U.

For example, the control parameter may include the actuation duration from when controller 120 starts actuating wakefulness inducer 300 to when controller 120 stops wakefulness inducer 300.

With this configuration, controller 120 automatically stops the wakefulness inducer when the actuation duration included in the control parameter has passed. Therefore, user U is less likely to become accustomed to the method executed by wakefulness inducer 300 to induce wakefulness even when user U has repeatedly used wakefulness inducer 300 connected to wakefulness induction control device 100. In other words, this configuration can suppress a decrease in the wakefulness inducing effect by making user U less likely to become accustomed to the wakefulness inducing method.

In addition, for example, the control parameter may include the current time. Controller 120 may change the mode in which wakefulness inducer 300 is actuated in accordance with the current time indicated by the control parameter.

With this configuration, for example, at a time such as an evening time when user U is presumably likely to become sleepy, an adjustment may be made so as to allow more wakefulness to be induced in the user. Therefore, this configuration can increase the wakefulness inducing effect on user U.

In addition, for example, the control parameter may further include the wakefulness level information indicating the degree of wakefulness for bringing the sleepiness level that indicates the degree of sleepiness of user U to a predetermined sleepiness level. For example, the wakefulness level information may include the stop reference information indicating the sleepiness level of user U at which wakefulness inducer 300 is to be stopped.

With this configuration, controller 120 can actuate wakefulness inducer 300 so as to induce wakefulness to a predetermined sleepiness level desired by user U.

As described above, wakefulness induction control device 100 may be connected to a plurality of wakefulness inducers 300 that differ in the wakefulness inducing method of inducting wakefulness in user U. To rephrase, wakefulness induction system 200 may include a plurality of wakefulness inducers 300 that differ in the wakefulness inducing method of inducing wakefulness in user U. In this case, when the sleepiness level detected by sleepiness detector 110 is equal to or higher than the first reference value, controller 120 actuates one or more wakefulness inducers 300 of the plurality of wakefulness inducers 300 in a mode corresponding to the environmental level.

With this configuration, wakefulness induction control device 100 can induce wakefulness in user U through a plurality of different wakefulness inducing methods. Accordingly, this configuration can suppress a decrease in the wakefulness inducing effect on user U since user U is less likely to become accustomed to the wakefulness inducing method.

Controller 120 may randomly select wakefulness inducer 300 to be actuated, for example. In addition, for example, controller 120 may select wakefulness inducer 300 to be actuated in accordance with the control parameter acquired by acquirer 160.

In addition, controller 120 may select one or more wakefulness inducers 300 to be actuated from a plurality of wakefulness inducers 300 in accordance with an attribute of user U and actuate selected wakefulness inducer(s) 300. For example, the attribute of user U is information such as the age, the gender, or the physique of user U. There is no particular limitation on the method through which controller 120 estimates the attribute of user U. For example, controller 120 may estimate the attribute of user U based on an image captured by imager 400. In addition, for example, acquirer 160 may acquire, as the control parameter, the attribute information pertaining to the attribute of user U. In this case, the control parameter may include information of the temperature, the music, the scent, or the like that user U desires. Controller 120 may select wakefulness inducer 300 to be actuated based on the estimated and/or acquired attribute of user U. With this configuration, controller 120 can actuate wakefulness inducer 300 that is estimated to have a high wakefulness inducing effect on user U.

In addition, if the sleepiness level of user U fails to reach or fall below the third reference value when the predetermined duration has passed after wakefulness inducer 300 has been actuated, controller 120 may actuate wakefulness inducer 300 different from wakefulness inducer 300 being actuated to induce wakefulness in user U.

Figure 13:
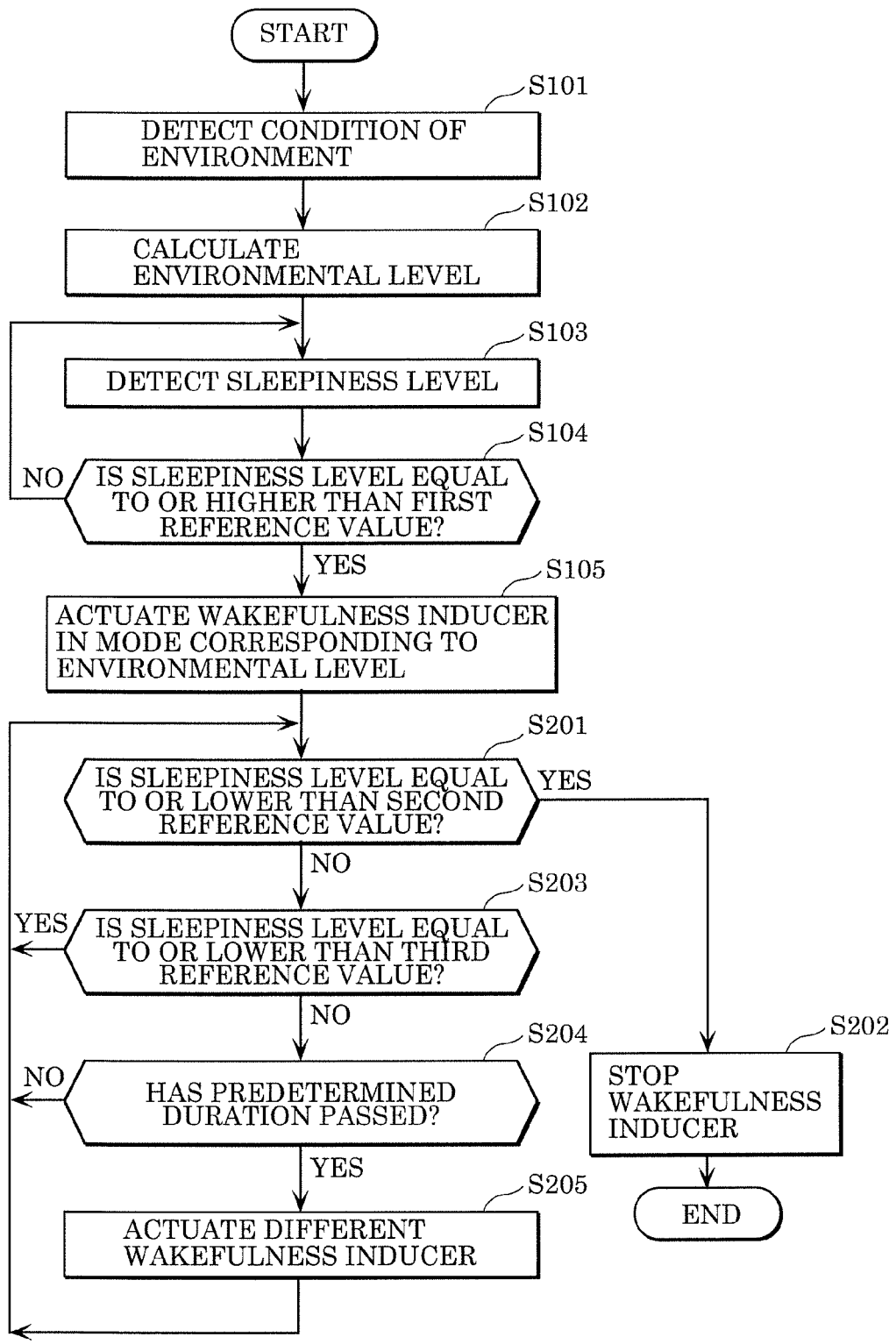
FIG. 13 is a flowchart illustrating another example of a procedure through which a wakefulness induction control device according to an embodiment actuates a wakefulness inducer.

FIG. 13 is a flowchart illustrating another example of a procedure through which wakefulness induction control device 100 according to the embodiment actuates wakefulness inducer 300.

First, environmental information detector 150, calculator 2, sleepiness detector 110, and controller 120 execute operations similar to those in step S101 to step S105 illustrated in FIG. 10.

Then, controller 120 determines whether the sleepiness level of user U detected by sleepiness detector 110 is equal to or lower than the second reference value (step S201).

When controller 120 has determined that the sleepiness level of user U is equal to or lower than the second reference value (YES in step S201), controller 120 stops wakefulness inducer 300.

Meanwhile, when controller 120 has determined that the sleepiness level of user U is neither equal to nor lower than the second reference value (NO in step S201), controller 120 determines whether the sleepiness level of user U is equal to or lower than the third reference value (step S203).

When controller 120 has determined that the sleepiness level of user U is equal to or lower than the third reference value (YES in step S203), controller 120 returns to step S201 and determines whether the sleepiness level of the user is equal to or lower than the second reference value.

Meanwhile, when controller 120 has determined that the sleepiness level of user U is neither equal to nor lower than the third reference value (NO in step S203), controller 120 determines whether the predetermined duration preset as desired has passed (step S204). For example, when wakefulness induction control device 100 includes a time tracker, such as an RTC, controller 120 may acquire information on whether the predetermined duration has passed from the RTC.

When controller 120 has determined that the predetermined duration has not passed (NO in step S204), controller 120 returns to step S201 and determines whether the sleepiness level of the user is equal to or lower than the second reference value.

Meanwhile, when controller 120 has determined that the predetermined duration has passed (YES in step S204), controller 120 actuates wakefulness inducer 300 that differs in the wakefulness inducing method from wakefulness inducer 300 being actuated (step S205).

After having actuated wakefulness inducer 300 that differs in the wakefulness inducing method from wakefulness inducer 300 having been actuated, controller 120 returns again to step S201 and continues with the determination as to whether the sleepiness level of user U is equal to or lower than the second reference value.

Figure 14:
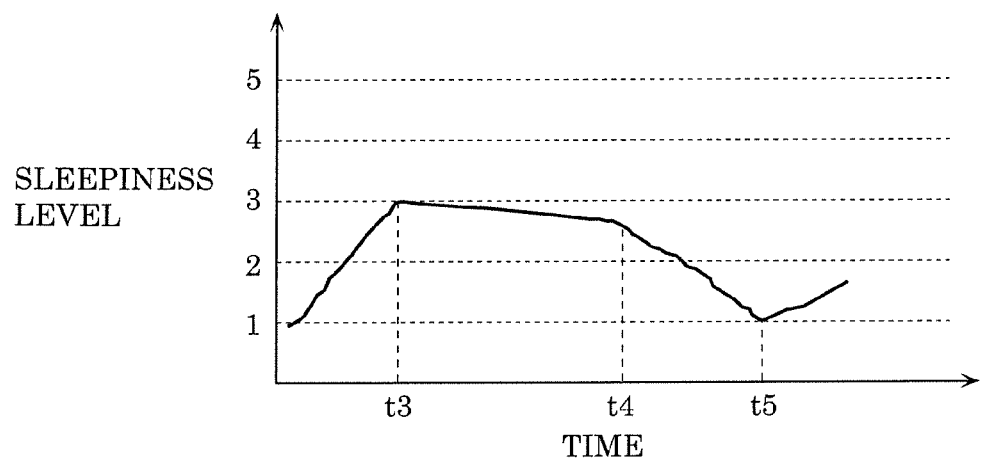
FIG. 14 illustrates another example of a change in the sleepiness level with respect to the time obtained when a wakefulness induction control device according to an embodiment is used.

FIG. 14 illustrates another example of a change in the sleepiness level with respect to the time obtained when wakefulness induction control device 100 according to the embodiment is used. In other words, FIG. 14 is a graph illustrating an example of a change in the sleepiness level of user U obtained when wakefulness induction system 200 is operated in accordance with the flowchart illustrated in FIG. 13. In the graph illustrated in FIG. 14, the horizontal axis represents the time, and the vertical axis represents the sleepiness level of user U.

As illustrated in FIG. 14, the sleepiness level of user U rises along with the passage of time. At time t3, the sleepiness level of user U reaches 3. At this point, controller 120 actuates wakefulness inducer 300 (step S105 indicated in FIG. 13).

However, the sleepiness level of user U may not decrease to the third reference value even with the passage of time. In other words, the wakefulness inducing method of wakefulness inducer 300 being actuated may not have a significant effect of inducing wakefulness in user U. In this case, at time t4, controller 120 actuates wakefulness inducer 300 that differs in the wakefulness inducing method from wakefulness inducer 300 being actuated (step S205 indicated in FIG. 13). In other words, in FIG. 14, the predetermined duration corresponds to the duration from time t3 to time t4.

As more time passes, the sleepiness level of user U gradually decreases. At time t5, controller 120 stops wakefulness inducer 300 since the sleepiness level of user U has reached or fallen below the second reference value.

In this manner, when the sleepiness level of user U fails to reach or fall below the third reference value for a predetermined duration, controller 120 actuates wakefulness inducer 300 that differs in the wakefulness inducing method from one or more wakefulness inducers 300 being actuated.

With this configuration, even when one wakefulness inducing method does not succeed in inducing wakefulness in user U, another wakefulness inducing method with a possibility of inducing wakefulness in user U can be executed. Accordingly, this configuration suppresses a failure in inducing wakefulness in user U.

Now, an operation of wakefulness induction control device 100 and wakefulness induction system 200 performed when there are a plurality of users in a given environment will be described.

Figure 15:
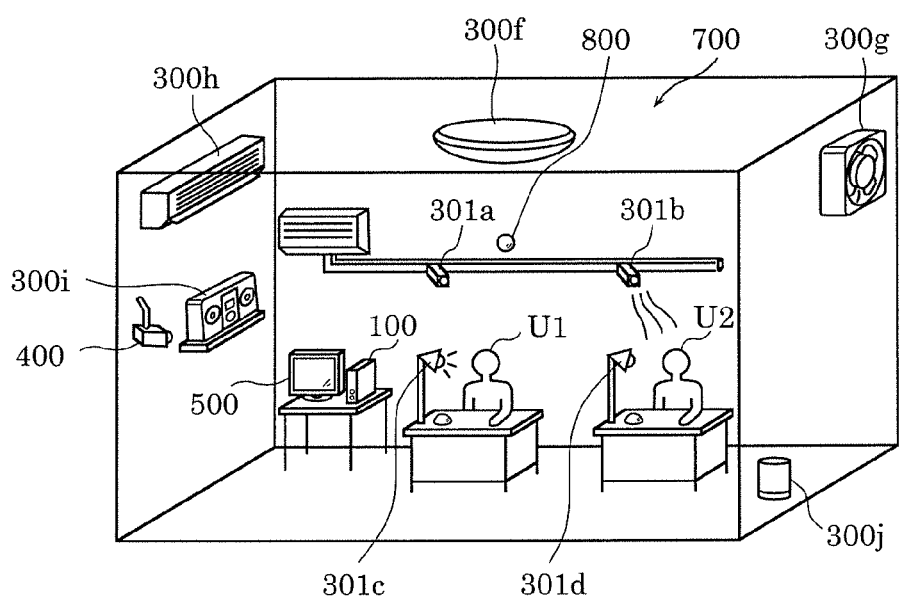
FIG. 15 is an illustration for describing a system including a wakefulness induction control device according to Variation 2 of an embodiment.

FIG. 15 is an illustration for describing a system including wakefulness induction control device 100 according to Variation 2 of an embodiment.

For example, wakefulness induction control device 100 and wakefulness induction system 200 are provided in vehicle 600 in FIG. 5. However, the environment in which wakefulness induction control device 100 and wakefulness induction system 200 are used is not limited to a vehicle. For example, wakefulness induction control device 100 and wakefulness induction system 200 may be used inside a room, such as an office. In addition, wakefulness induction control device 100 and wakefulness induction system 200 according to the present disclosure are applied also when there are a plurality of users in a given environment. FIG. 15 illustrates a case in which two users—user U1 and user U2—are present in room interior 700.

As illustrated in FIG. 15, wakefulness induction control device 100 is disposed in room interior 700. Wakefulness induction control device 100 is connected to a plurality of wakefulness inducers 300f to 300j that differ in the wakefulness inducing method via a wire (not illustrated) or the like. As with wakefulness inducers 300 (wakefulness inducers 300a to 300d) described above, examples of wakefulness inducers 300f to 300j include an acoustic device that emits a sound, an emission device that emits light, an aroma generator that produces a scent, and an air conditioner that controls the air conditioning, such as the temperature, the humidity, or the $CO_2$ concentration. In other words, wakefulness inducers 300f to 300j are devices that induce wakefulness by stimulating users U1 and U2 with a sound, light, heat, or the like or devices that lower the humidity, the $CO_2$ concentration, or the like to improve the environment causing the sleepiness in users U1 and U2.

In addition, wakefulness induction control device 100 is connected to individual wakefulness inducers (wakefulness inducers) 301a to 301d that can induce wakefulness individually in user U1 and user U2 via a wire (not illustrated) or the like. When there are a plurality of users (two users—user U1 and user U2—in FIG. 15, sleepiness detector 110 detects the sleepiness level of each of the users. Controller 120 actuates individual wakefulness inducers (wakefulness inducers) 301a to 301d for each of the users in accordance with the environmental level calculated by calculator 2 based on the environment detected by environmental information detector 150 and the sleepiness level of each of the users.

As with wakefulness inducers 300f to 300j described above, examples of individual wakefulness inducers 301a to 301d include an acoustic device that emits a sound, an emission device that emits light, an aroma generator that produces a scent, and an air conditioner that controls the air conditioning, such as the temperature, the humidity, or the $CO_2$ concentration. For example, individual wakefulness inducers 301a and 301b that control the air conditioning through sending the air that is likely to induce wakefulness in each user and individual wakefulness inducers 301c and 301d that employ light are used as the individual wakefulness inducers.

Figure 16:
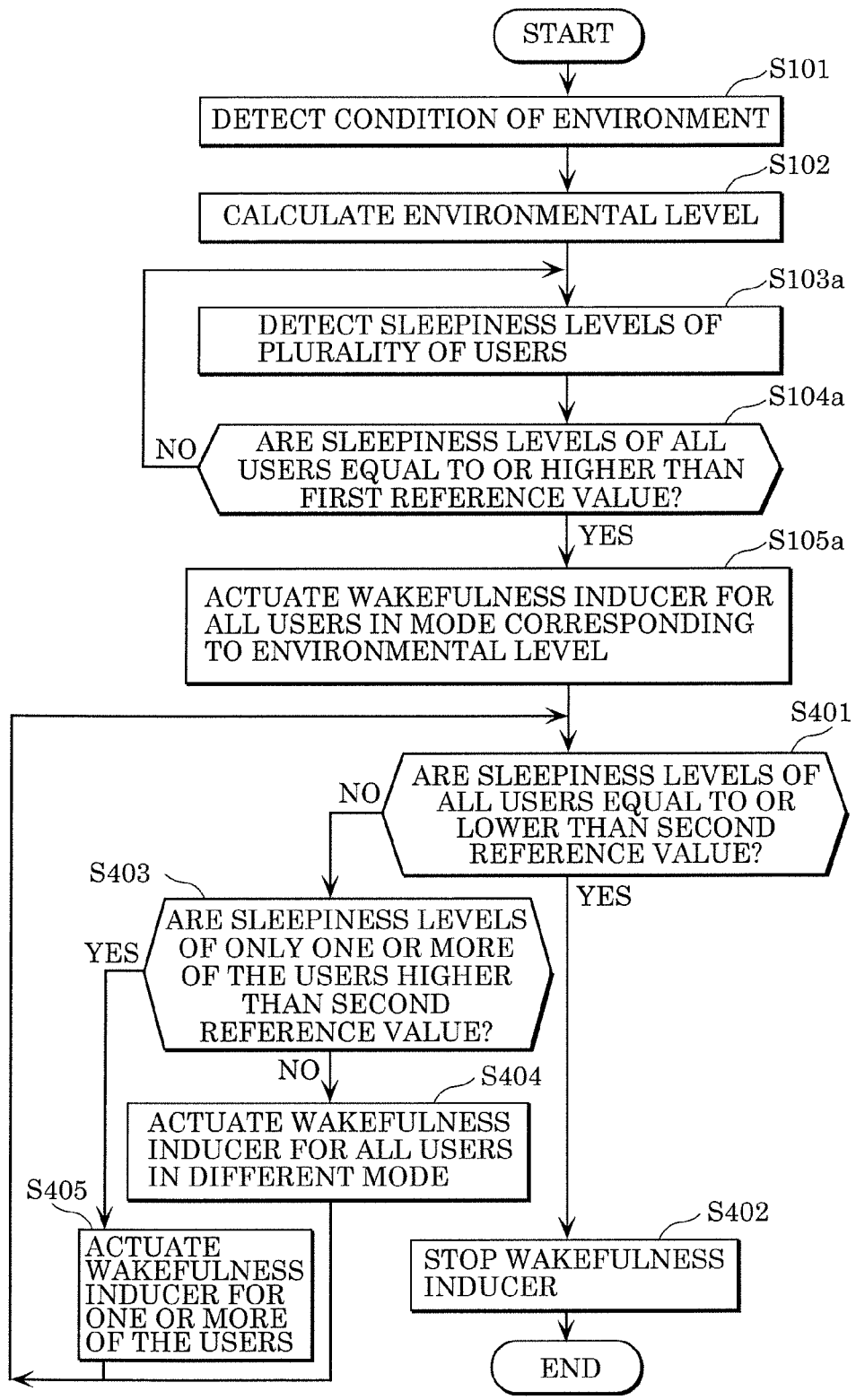
FIG. 16 is a flowchart illustrating an operation procedure through which a wakefulness induction control device according to Variation 2 of an embodiment actuates a wakefulness inducer when the wakefulness induction control device is used for a plurality of persons.

FIG. 16 is a flowchart illustrating an operation procedure through which wakefulness induction control device 100 actuates wakefulness inducers 300f to 300j and individual wakefulness inducers 301a to 301d when wakefulness induction control device 100 according to Variation 2 of the embodiment is used for a plurality of users.

Environmental information detector 150 detects the condition of the environment surrounding users U1 and U2 (step S101). Environmental information detector 150 outputs, to calculator 2, the condition, such as the brightness, the sound volume, or the temperature, of the environment surrounding users U1 and U2 and sensed by sensor 800 as the environmental information.

Then, calculator 2 calculates the environmental level based on the environmental information output by environmental information detector 150 (step S102). Calculator 2 outputs information including the calculated environmental level to controller 120.

Then, sleepiness detector 110 detects the sleepiness level of each of the plurality of users (step S103a). For example, sleepiness detector 110 detects the sleepiness level of each of users U1 and U2 by acquiring a moving image captured by imager 400 and analyzing the acquired moving image.

Then, controller 120 determines whether the sleepiness levels of all the users detected by sleepiness detector 110 are equal to or higher than the first reference value (step S104a). In other words, controller 120 determines whether the sleepiness levels of users U1 and U2 detected by sleepiness detector 110 are both equal to or higher than the first reference value.

When controller 120 has determined that the sleepiness levels of not all the users are equal to or higher than the first reference value (NO in step S104a), sleepiness detector 110 and controller 120 continue to execute the operations in step S103a and step S104a.

Meanwhile, when controller 120 has determined that the sleepiness levels of all the users are equal to or higher than the first reference value (YES in step S104a), controller 120 actuates a wakefulness inducer for all the users in a mode corresponding to the environmental level calculated by calculator 2 (step S105a). For example, controller 120 actuates wakefulness inducer 300g, which is a ventilation fan, and lowers the overall $CO_2$ concentration in room interior 700 to induce wakefulness in each of users U1 and U2. In addition, for example, controller 120 actuates wakefulness inducer 300j, which is an aroma generator, and controls the overall scent in room interior 700 to induce wakefulness in each of users U1 and U2.

Then, controller 120 determines whether the sleepiness levels of all the users detected by sleepiness detector 110 are equal to or lower than the second reference value (step S401). In other words, controller 120 determines whether the sleepiness levels of users U1 and U2 detected by sleepiness detector 110 are both equal to or lower than the second reference value.

When controller 120 has determined that the sleepiness levels of all the users are equal to or lower than the second reference value (YES in step S401), controller 120 stops the wakefulness inducer being actuated (step S402).

Meanwhile, when controller 120 has determined that the sleepiness levels of not all the users are equal to or lower than the second reference value (NO in step S401), controller 120 determines whether the sleepiness levels of only one or more of the users detected by sleepiness detector 110 are greater than the second reference value (step S403). In other words, controller 120 determines whether, of users U1 and U2 detected by sleepiness detector 110, the sleepiness levels of both users U1 and U2 are greater than the second reference value or the sleepiness level of one of users U1 and U2 is greater than the second reference value.

When controller 120 has determined that the sleepiness levels of all the users detected by sleepiness detector 110 are greater than the second reference value (NO in step S403), controller 120 actuates the wakefulness inducer in a different mode (step S404). For example, controller 120 actuates a wakefulness inducer that differs in the wakefulness inducing method from the wakefulness inducer being actuated. In addition, for example, when wakefulness inducer 300j, which is an aroma generator, is being actuated, controller 120 may cause wakefulness inducer 300j to intensify the scent to facilitate induction of wakefulness in each of users U1 and U2. Then, controller 120 returns to step S401 and determines whether the sleepiness levels of all the users are equal to or lower than the second reference value.

Meanwhile, when controller 120 has determined that the sleepiness levels of only one or more of the users detected by sleepiness detector 110 are higher than the second reference value (YES in step S403), controller 120 actuates a wakefulness inducer only for the one or more of the users with the sleepiness levels higher than the second reference value. For example, when the sleepiness level of user U1 is higher than the second reference value and the sleepiness level of user U2 is equal to or lower than the second reference value, controller 120 actuates individual wakefulness inducer 301a that controls the air conditioning so as to induce wakefulness only in user U1. Then, controller 120 returns to step S401 and determines whether the sleepiness levels of all the users are equal to or lower than the second reference value. This configuration makes it possible to continue with inducing wakefulness in user U1 whose sleepiness level has not decreased to the second reference value and to refrain from unnecessarily inducing wakefulness in user U2 whose sleepiness level has decreased to the second reference value.

In step S405, controller 120 may or may not stop the wakefulness inducer being actuated when actuating the individual wakefulness inducer.

In addition, in step S104a, although controller 120 determines whether the sleepiness levels of all the users detected by sleepiness detector 110 are equal to or higher than the first reference value, there is no particular limitation on that the sleepiness levels of all the users are equal to or higher than the first reference value. For example, controller 120 may determines whether the sleepiness levels of one or more of the users detected by sleepiness detector 110 are equal to or higher than the first reference value. In this case, when controller 120 has determined that the sleepiness levels of the one or more of the users are equal to or higher than the first reference value, controller 120 may actuate a wakefulness inducer for all the users in a mode corresponding to the environmental level calculated by calculator 2. For example, in a case in which there are five users in a given environment, controller 120 may actuate a wakefulness inducer when the sleepiness levels of four of the users are equal to or higher than the first reference value. In this case, in step S403, the condition based on which controller 120 actuates the individual wakefulness inducer may be changed. Specifically, in a case in which there are five users in a given environment and where controller 120 actuates a wakefulness inducer when the sleepiness levels of four of the users are equal to or higher than the first reference value, in step S403, controller 120 may actuate an individual wakefulness inducer for three of the users when the sleepiness levels of these three users are equal to or higher than the second reference value. In this manner, in the flowchart illustrated in FIG. 16, the condition of the sleepiness level and the condition of the number of users based on which controller 120 actuates a wakefulness inducer or an individual wakefulness inducer may be set as desired.

Figures 17A, 17B:
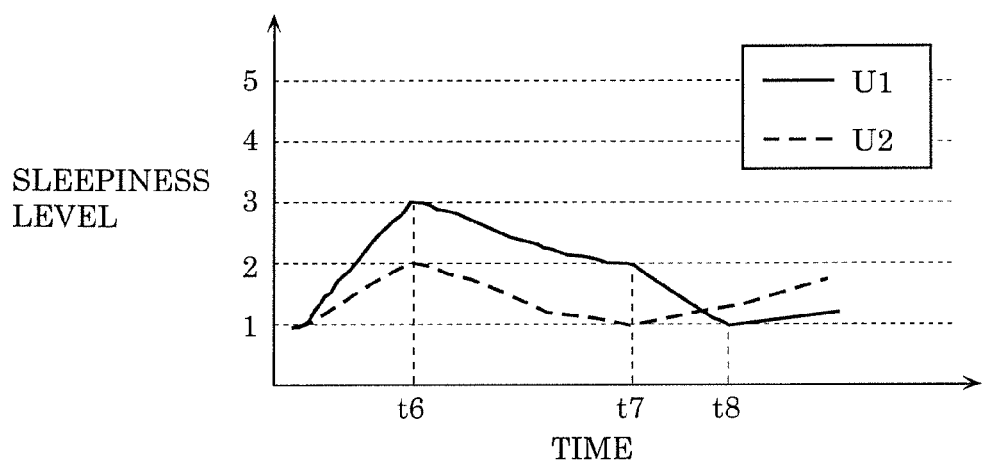
FIG. 17A illustrates an example of a change in the sleepiness level with respect to a wakefulness inducing method obtained when a wakefulness induction control device according to Variation 2 of an embodiment is used.
FIG. 17B illustrates an example of a change in the sleepiness level with respect to the time obtained when a wakefulness induction control device according to Variation 2 of an embodiment is used.

FIG. 17A illustrates an example of a change in the sleepiness levels of users U1 and U2 with respect to a wakefulness inducing method obtained when wakefulness induction control device 100 according to Variation 2 of the embodiment is used. FIG. 17B illustrates an example of a change in the sleepiness levels of users U1 and U2 with respect to the time obtained when wakefulness induction control device 100 according to Variation 2 of the embodiment is used. FIGS. 17A and 17B shows a graph illustrating an example of a change in the sleepiness levels of users U1 and U2 obtained when controller 120 has caused a wakefulness inducer and an individual wakefulness inducer to operate in accordance with the flowchart illustrated in FIG. 16. In FIG. 17B, the solid line indicates a change over time in the sleepiness level of user U1, and the dashed line indicates a change over time in the sleepiness level of user U2. In the graph illustrated in FIG. 17B, the horizontal axis represents the time, and the vertical axis represents the sleepiness level.

In the description on FIGS. 17A and 17B, a case in which the first reference value indicates that the sleepiness level is 2 and the second reference value indicates that the sleepiness level is 1 will be described.

As illustrated in FIG. 17B, the sleepiness levels of users U1 and U2 rise along with the passage of time. At time t6, the sleepiness levels of users U1 and U2 both reach 2 (the state of NO CONTROL indicated in FIG. 17A). At this point, controller 120 controls room interior 700 as a whole and actuates a wakefulness inducer for both users U1 and U2 (step S105a indicated in FIG. 16). For example, controller 120 actuates wakefulness inducer 300g, which is a ventilation fan, and lowers the overall $CO_2$ concentration in room interior 700 to induce wakefulness in each of users U1 and U2.

As more time passes, the sleepiness levels of users U1 and U2 gradually decrease. At time t7, the sleepiness level of user U2 reaches 1, but the sleepiness level of user U1 does not reach 1 (the state of $CO_2$ CONTROL ON in FIG. 17A). At this point, controller 120 controls an individual wakefulness inducer and induces wakefulness only in user U1 (step S405 illustrated in FIG. 16). For example, controller 120 actuates individual wakefulness inducer 301a, which controls the air conditioning, so as to induce wakefulness only in user U1.

As more time passes, the sleepiness level of user U1 gradually decreases. At time t8, controller 120 stops the individual wakefulness inducer since the sleepiness level of user U1 has reached 1 (the state of INDIVIDUAL TEMPERATURE CONTROL in FIG. 17A).

In this manner, when there are a plurality of users in a given environment, sleepiness detector 110 may detect the sleepiness level of each of the plurality of users. In this case, controller 120 stops the wakefulness inducer when the sleepiness level of each of the plurality of users is equal to or lower than the second reference value.

With this configuration, controller 120 can induce wakefulness in the plurality of users in the same environment to a predetermined sleepiness level. In other words, this configuration makes it possible to induce wakefulness in a number of users with ease even in an environment where there are a plurality of users.

In addition, controller 120 further actuates a wakefulness inducer for only one or more of the users when the sleepiness levels of only the one or more of the plurality of users are higher than the second reference value. There is no particular limitation on the method of actuating the wakefulness inducer individually. For example, when the sleepiness level of only user U1 illustrated in FIG. 15 is higher than the second reference value, controller 120 actuates individual wakefulness inducer 301a, which can send air only toward user U1, and/or individual wakefulness inducer 301c, which can illuminate only user U1 with light.

With this configuration, controller 120 can execute, for each user, a wakefulness inducing method suitable for each user even when wakefulness cannot be induced in a plurality of users present in the same environment to a predetermined sleepiness level through the same wakefulness inducing method. In other words, this configuration makes it possible to induce wakefulness through a wakefulness inducing method suitable for each user even in an environment where there are a plurality of users.

Other Embodiments

Thus far, a sleepiness estimating device, a wakefulness induction control device, and a wakefulness induction system according to the present disclosure have been described based on embodiments and variations, but the present disclosure is not limited to the embodiments and the variations described above. For example, an embodiment obtained by making various modifications that a person skilled in the art can conceive of to the foregoing embodiments and variations and an embodiment achieved by combining, as desired, the constituent elements and the functions in the embodiments and the variations within the scope that does not depart from the spirit of the present disclosure are also encompassed by the present disclosure.

For example, in the foregoing embodiment, the controller determines whether the sleepiness level detected by the sleepiness detector is equal to or higher than the first reference value, but this is not a limiting example. For example, the sleepiness detector may determine whether the detected sleepiness level is equal to or higher than the first reference value. In this case, the sleepiness detector outputs the determination result of the sleepiness level to the controller. Based on the determination result output by the sleepiness detector, the controller actuates the wakefulness inducer.

As described above, the controlling bodies in the control executed by constituent elements such as the environmental information detector, the calculator, the controller, and the sleepiness detector described above are merely examples, and there is no limitation thereon.

For example, the present disclosure can be implemented not only in the form of a sleepiness estimating device or a wakefulness induction control device but also in the form of a program that includes, as steps, the processes performed by the constituent elements of the sleepiness estimating device or the wakefulness induction control device or a recording medium, such as a computer readable digital versatile disc (DVD), having the program recorded therein. The program may be prerecorded in a recording medium or supplied to a recording medium via a broadband communication network including the internet.

In other words, the general or specific embodiments described above may be implemented in the form of a system, a device, an integrated circuit, a computer program, a computer readable recording medium, or any desired combination of a system, a device, an integrated circuit, a computer program, and a recording medium.

INDUSTRIAL APPLICABILITY

The present disclosure is used in a sleepiness estimating device that can quantitatively calculate, from an environment surrounding a person, the degree of how likely the person becomes sleepy in that environment as an environmental level and prompt the person to make an improvement or the like on the environment by outputting the calculated result. In addition, the present disclosure can be used as a wakefulness induction control device and a wakefulness induction system that include the sleepiness estimating device and that can induce wakefulness in the person more effectively in accordance with the environmental level calculated by the sleepiness estimating device. The present disclosure is used in, for example but not limited to, a device that is disposed in a vehicle, an office, or the like and induces wakefulness in a person by actuating an air conditioning device, an acoustic device, or the like.

The invention claimed is:

1. A wakefulness induction control device, comprising:
a sleepiness estimating device including,
an environmental information detector that detects a plurality of conditions of an environment surrounding a person and outputs environmental information indicating the conditions detected of the environment,
a calculator that calculates an environmental level indicating a degree of how likely the person becomes sleepy in the environment in accordance with the environmental information output by the environmental information detector, and
an output that outputs the environmental level calculated by the calculator;
a controller;
a wakefulness inducer that induces wakefulness in the person in a mode corresponding to the environmental level; and
a sleepiness detector that detects a sleepiness level indicating a degree of sleepiness of the person, wherein
the controller actuates the wakefulness inducer when the sleepiness level detected by the sleepiness detector is equal to or higher than a first reference value, and
when there are a plurality of persons in the environment,
the sleepiness detector detects the sleepiness level of each of the plurality of persons, and
the controller stops the wakefulness inducer when the sleepiness level of each of the plurality of persons is equal to or lower than a second reference value.

2. The wakefulness induction control device according to claim 1, wherein when the sleepiness level of only one or more of the plurality of persons is higher than the second reference value, the controller actuates the wakefulness inducer only for the one or more of the plurality of persons.

3. The wakefulness induction control device according to claim 1, further comprising:
an acquirer that acquires a control parameter for controlling the wakefulness inducer, wherein
the controller actuates the wakefulness inducer in a mode corresponding to the control parameter acquired by the acquirer.

4. The wakefulness induction control device according to claim 3, wherein the control parameter includes an actuation duration from when the controller starts actuating the wakefulness inducer to when the controller stops the wakefulness inducer.

5. The wakefulness induction control device according to claim 3, wherein
the control parameter includes a current time, and
the controller changes the mode in which the wakefulness inducer is actuated in accordance with the current time indicated by the control parameter.

6. The wakefulness induction control device according to claim 3, wherein the control parameter includes wakefulness level information indicating a degree of wakefulness for bringing a sleepiness level indicating a degree of sleepiness of the person to a predetermined sleepiness level.

7. The wakefulness induction control device according to claim 1, wherein
the wakefulness induction control device is connected to a plurality of wakefulness inducers that differ in a wakefulness inducing method of inducing wakefulness in the person, and
the controller actuates one or more wakefulness inducers of the plurality of wakefulness inducers in the mode corresponding to the environmental level.

8. The wakefulness induction control device according to claim 7, wherein when the sleepiness level of the person indicating the degree of sleepiness of the person fails to reach or fall below a third reference value for a predetermined duration, the controller actuates a wakefulness inducer that differs in a wakefulness inducing method from the one or more wakefulness inducers being actuated.

9. A wakefulness induction system, comprising:
the wakefulness induction control device according to claim 1; and
the wakefulness inducer.

10. A wakefulness induction control device, comprising:
a controller;
a wakefulness inducer that induces wakefulness in a person in a mode corresponding to
a environmental level; and
a sleepiness detector that detects a sleepiness level indicating a degree of sleepiness of the person, wherein
the controller actuates the wakefulness inducer when the sleepiness level detected
by the sleepiness detector is equal to or higher than a first reference value, and
when there are a plurality of persons in an environment,
the sleepiness detector detects the sleepiness level of each of the plurality
of persons, and
the controller stops the wakefulness inducer when the sleepiness level of
each of the plurality of persons is equal to or lower than a second reference value.

11. A wakefulness induction control device according to claim 10 further comprising:
a sleepiness estimating device including,
an environmental information detector that detects a plurality of conditions of the
environment surrounding the person and outputs environmental information indicating the conditions detected of the environment,
a calculator that calculates an environmental level indicating a degree of how
likely the person becomes sleepy in the environment in accordance with the
environmental information output by the environmental information detector, and
an output that outputs the environmental level calculated by the calculator.

12. The wakefulness induction control device according to claim 11, wherein when the sleepiness level of only one or more of the plurality of persons is higher than the second reference value, the controller actuates the wakefulness inducer only for the one or more of the plurality of persons.

13. The wakefulness induction control device according to claim 11, further comprising:
an acquirer that acquires a control parameter for controlling the wakefulness inducer,
wherein the controller actuates the wakefulness inducer in a mode corresponding to the control parameter acquired by the acquirer.

14. The wakefulness induction control device according to claim 13, wherein
the control parameter includes an actuation duration from when the controller starts actuating the wakefulness inducer to when the controller stops the wakefulness inducer.

15. The wakefulness induction control device sccording to claim 13, wherein
the control parameter includes a current time, and
the controller changes the mode in which the wakefulness inducer is actuated in
accordance with the current time indicated by the control parameter.

16. The wakefulness induction control device according to claim 13, wherein the control parameter includes wakefulness level information indicating a degree of wakefulness for bringing a sleepiness level indicating a degree of sleepiness of the person to a predetermined sleepiness level.

17. The wakefulness induction control device according to claim 11, wherein
the wakefulness induction control device is connected to a plurality of wakefulness
inducers that differ in a wakefulness inducing method of inducing wakefulness in the person, and
the controller actuates one or more wakefulness inducers of the plurality of wakefulness
inducers in the mode corresponding to the environmental level.

18. The wakefulness induction control device according to claim 17, wherein when the sleepiness level of the person indicating the degree of sleepiness of the person fails to reach or fall below a third reference value for a predetermined duration, the controller actuates a wakefulness inducer that differs in a wakefulness inducing method from the one or more wakefulness inducers being actuated.

19. A wakefulness induction system, comprising:
the wakefulness induction control device according to claim 10; and
the wakefulness inducer.

* * * * *